US 8,715,936 B2

(12) United States Patent
Gygax et al.

(10) Patent No.: US 8,715,936 B2
(45) Date of Patent: May 6, 2014

(54) **METHOD OF DETERMINING TYPES I, II, III, IV OR V OR METHICILLIN-RESISTANT *STAPHYLOCOCCUS AUREUS* (MRSA) IN A BIOLOGICAL SAMPLE**

(75) Inventors: Scott E. Gygax, Yardley, PA (US); Christina Lim Overmyer, Edison, NY (US); Lisa A. DeSalvia, Glenwood, NJ (US); Martin E. Adelson, East Wiindsor, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 332 days.

(21) Appl. No.: 12/930,663

(22) Filed: Jan. 13, 2011

(65) Prior Publication Data
US 2011/0312876 A1 Dec. 22, 2011

Related U.S. Application Data

(60) Provisional application No. 61/335,874, filed on Jan. 13, 2010.

(51) Int. Cl.
*C12Q 1/68* (2006.01)
*C12P 19/34* (2006.01)
*C07H 21/04* (2006.01)

(52) U.S. Cl.
USPC ............... 435/6.12; 435/91.2; 536/24.33

(58) Field of Classification Search
None
See application file for complete search history.

(56) References Cited

U.S. PATENT DOCUMENTS

| 6,156,507 | A | 12/2000 | Hiramatsu |
| 2006/0252069 | A1 | 11/2006 | Zhang |
| 2006/0252078 | A1 | 11/2006 | Huletsky |
| 2007/0082340 | A1 | 4/2007 | Huletsky |
| 2008/0220428 | A1 | 9/2008 | Aichinger |
| 2008/0227087 | A1 | 9/2008 | Huletsky |
| 2011/0151452 | A1* | 6/2011 | Jean et al. .......... 435/6.11 |

OTHER PUBLICATIONS

Lowe et al., A computer program for selection of oligonucleotide primers for polymerase chain reactions. Nucleic Acids Research, vol. 18, No. 7, pp. 1757-1761, 1990.*
Kramer, Fred Russel, et al., "Molecular Beacons: Probes that Fluoresce upon Hybridization," Nature Biotechnology, Mar. 1996, vol. 14, Nature Publishing Group.
Wittwer, C.T., et al., "The LightCycler: A Microvolume Multisample Fluorimeter with Rapid Temperature Control," Biotechniques, Jan. 1997, vol. 22, No. 1, 176-181.

* cited by examiner

*Primary Examiner* — Prabha Chunduru
(74) *Attorney, Agent, or Firm* — Siu K. Lo

(57) ABSTRACT

Disclosed are diagnostic methods for determining a subtype of methicillin-resistant *Staphylococcus aureus* (MRSA) in a biological sample of a mammal. Methods include providing a biological sample of the mammal, performing a PCR analysis of the biological sample, and analyzing the PCR amplicons with respect to their sizes so as to determine for type I, type II, type III, type IV or type V MRSA that may be present in the biological sample. Further example embodiments include using at least one mecA primer pair and/or using at least one *Staphylococcus aureus* nuc primer pair in the PCR analysis. Further disclosed are methods for screening populations for MRSA, and methods of treating a mammal testing positive for Type IV MRSA. Also disclosed are kits for determining a MRSA subtype in a mammal and isolated primers that may be used in the present methods and kits.

17 Claims, 27 Drawing Sheets

FIG. 2

(SA0022 gene)
33241 caaagttcaa gcccagaagc gatgtttgta ttattagcag gtataggttt aatcg<u>cgact</u>
       >>>> 5'orf0022 >>>>>>>                                        >>>>>

33301 <u>gtacgacgta gaaaagctag ctaa</u> (SA0022 stop)

5'UTR  aatata ttgaaaataa tactactgta tttcttaaat
33361 agaggtacg gtagtgtttt tttatgaaaa aaagcgataa ccgttgataa atatgggata
33421 taaaaacgag gataagtaat aagacatcaa ggtgtttatc cacagaaatg gggatagtta
33481 tccagaattg tgtacaattt aaagagaaat acccacaatg cccacagagt tatccacaaa
                                                         >>>>>>>>>>>>>
33541 tacacaggtt atacactaaa aatcgggcat aaatgtcagg aaaatatcaa aaactgcaaa
       >>>>>>>>>> 5'UTR 5 >>>>>>>>>>
              >>>> 5'UTR 4 >>>>>>>                     >>>> 5'UTR 3 >>>
33601 aaatattggt ataataagag ggaacagtgt gaacaagtta ataa<u>cttgtg gataactgga</u>
       >>>>>>
              >>>>>>>>> 5'UTR 2 >>>>>>>>>>>>>
              >>>>>>>>> 5'UTR 1 >>>>>>>>>>>>>>>>>>

33661 <u>aagttgataa ca atttgag gaccaaacga c</u>
       <b>atg</b>aaaatc accatttag ctgtagggaa
33721 actaaaagag aaatattgga agcaagccat agcagaatat gaaaaacgtt taggcccata
33781 caccaagata gacatcatag aagttccaga aaaaagca ccagaaaata tgagtgacaa
33841 agaaattgag caagtaaaag aaaaagaagg ccaacgaata ctagccaaaa tcaaaccaca
33901 atccacagtc attacattag aaatacaag aagatgcta tcttccgaag gattggccca
33961 agaattgaac caacgcatga cccaaggca agcgactt gttttcgtca ttgcggatc
34021 aaacggcctg cacaaggacg tcttacaacg cagtaactac gcactatcat tcagcaaaat
34081 gacattccca catcaaatga tgcgggttgt gttaattgaa caagtgtaca gagcatttaa
34141 gattatgcga gga <b>[MecDNA integration site]</b> gaggcgt atcataagta a <b>(<i>orfx</i> stop)</b>

FIG. 2 (Cont'd)

```
3'UTR aactaaaaa a [SCCmec type V]ttctgtatg aggagataat
34201 aatttggagg gtgttaaatg gtggacatta aatccacgtt cattcaatat ataagatata
34261 tcacgataat tgcgcatata acttaagtag tagctaacag ttgaaattag gccctatcaa
34321 attggtttat atctaaaatg attaatatag aatgcttctt tttgtcctta ttaaattata
34381 aaagtaactt tgcaatagaa acagttattt cataatcaac agtcattgac gtagctaagt
34441 aatgataaat aatcataaat aaaattacag atattgacaa aaaatagtaa atataccaat
34501 gaagtttcaa aagaacaatt ccaagaaatt gagaatgtaa ataataaggt caaagaattt
34561 tattaagatt tgaaagagta tcaatcaaga aagatgtagt tttttaataa actatttgga
34621 aaataattat cataatttaa aaactgacaa tttgcgagac tcataaaatg taataatgga
34681 aatagatgta aaatataatt aagggtgta at (SA0024 start) atgaagat taatatttat aaatctattt ataattttca ggaaacaaat 34761
```

FIG. 3

(strain: NCTC10442; Accession: AB033763)

38367 bp
```
accaaataat atccatcctt tgtttctttt gttatattct catcatatat tgaaatccaa ggaactttac tatagttccc
agtagcaacc ttccctacaa ctgaatattt atcttctttt atatgcactt ttaactgctt gggtaactta tcatggacta
aagttttata tagatcacct ttatcccaat cagattttt aactacatta ttggtacgtt tctctttaat taatttaagg
acctgcataa agttgctat catttgaaat tccctcctat tataaaatat attatgtctc attttcttca atatgtactt
                                                                        >>>>>> mec124c >
atttatattt taccgtaatt tactatattt agttgcagaa agaattttct caaagctaga actttgcttc actataagta
>>>>>                                                    >>>>>>>> mec124b >>>>>>>
                                                                         >>>>>>>> mec124a >>
ttcagtataa agaatatttc gctattattt acttgaaatg aaagactgcg gaggctaact atgtcaaaaa tcatgaacct
>>>>>>>>>>>
cattacttat gataagcttc
```
38867bp (Primers located downstream of the 5'orfX-mecDNA junction)

FIG. 4

(strain: N315; Accession: D86934)

57737 bp
gaatatttat cttcttttat atgcactttt aactgcttgg gtaacttatc atggactaaa gtttttatata gatcaccttt
atcccaatca gatttttttaa ctacattatt ggtacgtttc tctttaatta atttaaggac ctgcataaag ttgtctatca
tttgaaattc cctcctatta taaaatatat tatgtctcat tttcttcaat atgtacttat ttatattta ccgtaattta
                                                        >>>>>> mec124c >>>>>>>
ctatatttag ttgcagaaag aatttttctca aagctagaac tttgcttcac tataagtatt cagtataaag aatatttcgc
            >>>>>>>> mec124b >>>>>>>
                                    >>>>>>>>>>> mec124a >>>>>>>>>>>
tattatttac ttgaaatgaa agactgcgga ggctaactat gtcaaaaatc atgaacctca ttacttatga taagcttctt
aaaacataa cagcaattca cataaacctc atatgttctg atacattcaa aatcccttta tgaagcggct gaaaaaaccg
catcatttat gatatgcttc 58237bp (Primers located downstream of the 5'orfX-mecDNA junction)

FIG. 5

(strain: 85/2082; Accession: AB037671)

67294 bp
aaatcaaaaa taacatacct tacaactttt accgtcgata tcaattgctc ttttcttaat ttaggattgc tttcaaattt
tgtactataa cgtgaaacta cttttccttc tttataatta aaatttacta attcacaatc attttactt ccattacaa
aaacatccac tgttctaac acaaaatcta ataaacttcc tttattaat cgtaggcatt gtatatttcc tttcattctt
tcttgattcc attagtttaa atttaaaatt tcatccatca atttcttaat ttaattgtag ttccataatc aatataattt
                                                                >>>>>>>>>>>>>>>>> gtacagttat tatatattct agatcatcaa tagttgaaaa atggtttatt aaacactcta taaacatcgt atgatattgc
> mec3b >>>>  >>>>>>>>>>>>>> mec3a >>>>>>>>>>>>>>>
aaggtataat ccaatatttc atatatgtaa ttcctccaca tctcattaaa tcttaaatt atacacaacc taatttttag
ttttatttat gatacgcttc 67794bp (Primers located downstream of the 5'*orfX*-mecDNA junction)

FIG. 6

(strain: CA05; Accession: AB063172)

24722 bp
gaatatttat cttcttttat atgcactttt aactgcttgg gtaacttatc atggactaaa gttttatata gatcacctt
atcccaatca gattttttaa ctacattatt ggtacgtttc tcttaatta atttaaggac ctgcataaag ttgtctatca
tttgaaattc cctcctatta taaaatatat tatgtctcat tttcttcaat atgtacttat ttatattta ccgtaattta
>>>>>> mec124c >>>>>>>>
ctatatttag ttgcagaaag aatttctca aagctagaac tttgcttcac tataagtatt cagtataaag aatatttcgc
>>>>>>> mec124b >>>>>>>
>>>>>>>>>>>> mec124a >>>>>>>>>
tattatttac ttgaaatgaa agactgcgga ggctaactat gtcaaaaatc atgaacctca ttacttatga taagcttctt
aaaaacataa cagcaattca cataaacctc atatgttctg atacattcaa aatcccttta tgaagcggct gaaaaaaccg
catcatttat gatatgcttc 25222bp (Primers located downstream of the 5'orfX-mecDNA junction)

FIG. 7

(Strain: JSCC 3624 (WIS) — WBG8318; Accession: AB121219 rev. complement)

ataaaaagca ttaactggat ctttgtcagc attcctcttc tgcttaacca cattactacc tatttcaaat ctttctctag
cttcatttag tctgatattc attttattgt aaattcttc tttgaatgc ttaagttcac tatttttccg agtaataaaa
tttctaaac tatttatagc gctatttaaa tgcttaattt ggtcactatg atttatagat tcttctccaa taaccaaatt
>>>> mec5b >>>>>>>>>              >>>>>>>>> mec5a >>>>>>>>>>>                        >>>
cacaccatct atttcttcaa cttcttcaat attattttt aagtaaccag tattaaagat aacactttt tcattatcta
gtcttcttaa ccattcactt aatgagcttt ttccactccc atttcttcca aaaaatatat ttactttagt caaatcatct
tcactagtgt aattatcgaa tgatttataa ctaacatttt ctaatttatt taacataaaa tcaatccttt ttatatttaa
aatatattat acacaatccg (Primers located downstream of the 5'orfX-mecDNA junction)

FIG. 8

```
                    >>>>>> mecl24c >>>>>>>
AB033763 (Type I)   5' caaagctaga actttgcttc actataagta ttcagtataa agaatatttc gctattattt
D86934   (Type II)  5' caaagctaga actttgcttc actataagta ttcagtataa agaatatttc gctattattt
AB063172 (Type IV)  5' caaagctaga actttgcttc actataagta ttcagtataa agaatatttc gctattattt >>>>>>>> mecl24b >>>>>>>
                    >>>>>>>>>> mecl24a >>>>>>>>>>>
acttgaaatg aaagactgcg gaggctaact atgtcaaaaa tcatgaacct cattacttat gataagcttc ----------
acttgaaatg aaagactgcg gaggctaact atgtcaaaaa tcatgaacct cattacttat gataagcttc ttaaaaacat
acttgaaatg aaagactgcg gaggctaact atgtcaaaaa tcatgaacct cattacttat gataagcttc ttaaaaacat ---------- ---------- ---------- ---------- ---------- ---------- cgcatcattt
aacagcaatt cacataaaacc tcatatgttc aaaatccctt tatgaagcgg ctgaaaaaac cgcatcattt
aacagcaatt cacataaaacc tcatatgttc aaaatccctt tatgaagcgg ctgaaaaaac cgcatcattt ---------- -- 3'  (5' orfX mecDNA junction)
atgatatgct tc 3'  (5' orfX mecDNA junction)
atgatatgct tc 3'  (5' orfX mecDNA junction)
```

AB033763 - SEQ ID NO: 32
D86934 - SEQ ID NO: 33
AB063172 - SEQ ID NO: 35

FIG. 9

```
                                     >>>>>> mec124c >>>>>>>
AB033763 (Type I)   5' caaagctaga actttgcttc actataagta ttcagtataa agaatatttc gctattattt
D86934   (Type II)  5' caaagctaga actttgcttc actataagta ttcagtataa agaatatttc gctattattt
AB063172 (Type IV)  5' caaagctaga actttgcttc actataagta ttcagtataa agaatatttc gctattattt
AB037671 (Type III) 5' tcatccatca atttcttaat ttaattgtag ttccataatc aatataattt gtacagttat >>>>>>> mec124b >>>>>>>
                            >>>>>>>>>> mec124a >>>>>>>>>>
acttgaaatg aaagactgcg gaggctaact atgtcaaaaa tcatgaacct cattacttat gataagcttc ----------
acttgaaatg aaagactgcg gaggctaact atgtcaaaaa tcatgaacct cattacttat gataagcttc ttaaaaacat
acttgaaatg aaagactgcg gaggctaact atgtcaaaaa tcatgaacct cattacttat gataagcttc ttaaaaacat
tatatattct agatcatcaa tagttgaaaa atggtttatt aaacactcta taaacatcgt atgatattgc aaggtataat
                                                                >>>>>>>>>>>> mec3b >>>>>>
---------- ---------- ---------- ---------- ---------- ---------- ---------- ----------
aacagcaatt cacataaacc tcatatgttc tgatacattc aaaatccctt tatgaagcgg ctgaaaaaac cgcatcattt
aacagcaatt cacataaacc tcatatgttc tgatacattc aaaatccctt tatgaagcgg ctgaaaaaac cgcatcattt
atccaatatt tcatatatgt aattcctcca catctcatta aatttttaaa ttatacacaa cctaatttt agtttattt
>>>>            >>>>>>>>>>>>>>>>>> mec3a >>>>>>>>>>>>>>
---------- ---------- '3
atgatatgct tc'3
atgatatgct tc'3
atgatacgct tc'3

AB033763 - SEQ ID NO: 32
                D86934  - SEQ ID NO: 33
                AB063172 - SEQ ID NO:35
                AB037671 - SEQ ID NO: 34
```

FIG. 14

```
                                                                                                        >>>>>>>>>>
                                                                      >>>>>>>>>>
AB063172 (IVa)  1447bp  t aagaaagg atc|t|aacata atgcaacaac ttaaaacaaa acgtgtcggt atctatgtac
AB097677 (IVd)  1447bp  t aagaaagg atc|t|aacata atgcaacaac ttaaaacaaa acgtgtcggt atctatgtac
D86937   (IIa)  1447bp  c aagaaagg atc|a|aacata atgcaacaac ttaaaacaaa acgtgtcggt atctatgtac
AJ810120 (IIe)  1447bp  c aagaaagg atc|a|aacata atgcaacaac ttaaaacaaa acgtgtcggt atctatgtac ccrAB-F4>>>>>
gtgtatcaac agaaatgcaa agcacagaag gttatagtat cgacggacaa atcaatcaaa tcaaagaata ctgtgacttc
gtgtatcaac agaaatgcaa agcacagaag gttatagtat cgacggacaa atcaatcaaa tcaaagaata ctgtgacttc
gtgtatcaac agaaatgcaa agcacagaag gttatagtat cgacggacaa atcaatcaaa tcaaagaata ctgtgacttc
gtgtatcaac agaaatgcaa agcacagaag gttatagtat cgacggacaa atcaatcaaa tcaaagaata ctgtgacttc >>>>>>ccrAB-F3>>>>>>>>          >>>>>>ccrAB-F2>>>>>>
catcattttg aagttaaaga tatatacgct gatcgtggta tttcaggtaa atctatgad|a|acctgagc tccaacgtat
catcattttg aagttaaaga tatatacgct gaccgtggta tttcaggtaa atctatgad|a|acctgagc tccaacgtat
catcattttg aagttaaaga tatatacgct gaccgtggta tttcaggtaa atctatgad|c|acctgagc tccaacgtat
catcattttg aagttaaaga tatatacgct gaccgtggta tttcaggtaa atctatgad|t|cacctgagc tccaacgtat
catcattttg aagttaaaga tatatacgct gaccgtggta tttcaggtaa atctatgad|c|cacctgagc tccaacgtat >>>>>>ccrAB-F1>>>>>>>
         g ttgaa|a|gat gd|a|atataga ttgtgttatg atctacaaaa caaaccgatt agctcgtaat acatcggatc
         g ttgaa|a|gat gd|a|atatcga ctgtgttatg gtatacaaaa caaaccgatt agctcgtaat acatctgatc
         g attgaa|g|gat gd|t|tatcga ctgtgttatg gtctacaaaa caaaccgatt agctcgtaat acatctgatc
         g attgaa|g|gat gd|t|tatcga ctgtgttatg gtctacaaaa caaaccgatt agctcgtaat acatctgatc ttctgaaat cgtcgaagat ttgcataaac atttttcagt attttttcagt ttgtcagagc gtatggaagt caatacttq|t|
ttctcaaat tgtcgaagat ttacacaaac attttttcagt attttttcagt ttgtcagagc gtatggaagt caatacttq|t|
ttctcaaat tgtcgaagat ttacacaaac attttttcagt attttttcagt ttatcagagc gtatggaagt caatacttq|a|
ttctcaaat tgtcgaagat ttacacaaac attttttcagt attttttcagt ttatcagagc gtatggaagt caatacttq|a|
```

AB063172 - SEQ ID NO: 37
AB097677 - SEQ ID NO: 38
D86937 - SEQ ID NO: 39
AJ810120 - SEQ ID NO: 40

FIG. 14 (Cont'd)

```
tcttgtacac tcatgttaca aatacttgcg agtttctcag aattcgaacg taataacatt gtcgagaatg tatttatggg
tcttgtacac tcatgttaca gatacttgcg agtttctcag aattcgaacg taataacatt gtcgagaacg tatttatggg
tgggtacgc  tcatgttaca aatacttgcg agtttctcag aattcgaacg taataacatt gtcgagaatg tatttatggg
tgggtacgc  tcatgttaca aatacttgcg agtttctcag aattcgaacg taataacatt gtcgagaatg tatttatggg
tgggtacgc  tcatgttaca aatacttgcg agtttctcag aattcgaacg taataacatt gtcgagaatg tatttatggg gcaaacgaga cgtgcccaag aaggctatta tcaaggcaat ttacactag  aataccagat agtaaacacg
                                                                           >>>>>>>  <<<<<<<
tcaaacgaga cgtgcccaag aaggctatta tcaaggcaat ttacactag  aataccagat agtaaacacg
tcaaacgaga cgtgcccaag aaggctatta tcaaggcaat ttgcgttg   aataccatat agtaaacatg
tcaaacgaga cgtgcccaag aaggctatta tcaaggcaat ttgcgttg   aataccatat agtaaacatg
tcaaacgaga cgtgcccaag aaggctatta tcaaggcaat ttgcgttg   aataccatat agtaaacatg >ccrAB-F5>>>>>>
<ccrAB-R1<<<<<
agctactgat tadcaacat gaagctaata ttgtabaata tatattcgag tcctatgcca aaggabatgg ctatcgtaaa
agctactgat tadcaacat gaagctaata ttgtabaata tatattcgag tgctatgcca aaggabatgg ctatcgtaaa
aatgatgat  taatcaacat gaagctaata ttgtgcgttg tatattcgag tcctatgcca aagccatgg  ctatcgtaaa
aatgatgat  taatcaacat gaagctaata ttgtgcgttg tatattcgag tcctatgcca aagccatgg  ctatcgtaaa
aatgatgat  taatcaacat gaagctaata ttgtgcgttg tatattcgag tcctatgcca aagccatgg  ctatcgtaaa <<<<<<ccrAB-R2<<<<<<<
atagccaatg cattgaatca caaaggctat gtcactaaaa agggtaaacc ttttagtatt agttctatca catatatatt
attgccaatg cattgaatca caaaggatat gtcactaaaa agggaaaacc tttcagtatt agttcaatca catacatctt
atagccaatg cattaatca  caaaggctat gtcactaaaa agggtaaacc ttttagtatt agttctatca catatatatt
atagccaatg cattaatca  caaaggctat gtcactaaaa agggtaaacc ttttagtatt agttctatca catatatatt
atagccaatg cattaatca  caaaggctat gtcactaaaa agggtaaacc ttttagtatt agttctatca catatatatt <<<<<<<<ccrAB-R3<<<<<<<
agctaaccca ttctatatcg gcaaaattca atttgcgaaa tacaaagatt ggagtgaaaa acgtcgtaaa gggctgaatg
agctaaccct ttctatatcg gcaaaattca atttgcgaaa tacaaagatt ggagtgaaaa acgtcgtaaa gggctgaatg
agctaaccca ttctatatcg gcaaaattca atttgcgaaa tacaaagatt ggagtgaaaa acgtcgtaaa gggcttaatg
agctaaccca ttctatatcg gcaaaattca atttgcgaaa tacaaagatt ggagtgaaaa acgtcgtaaa gggcttaatg
agctaaccca ttctatatcg gcaaaattca atttgcgaaa tacaaagatt ggagtgaaaa acgtcgtaaa gggcttaatg
```

FIG. 14 (Cont'd)

```
ataaaccagt gatagctgaa ggtaagcatt ccccattat taatcaagat ttatgggata aagtacaaat gcgtaaaaaa
ataaaccagt gatagctgaa ggtaagcatt ccccattat taatcaagat ttatgggata aagtacaaat gcgtaagaaa
ataaaccagt gatagctgaa ggtaagcatt ccccattat taatcaagat ttatgggata aagtacaaat gcgtaaaaaa
ataaaccagt gatagctgaa ggtaagcatt ccccatttt taatcaagat ttatgggata aagtacaaat gcgtaaaaaa caagtcagtc aaaaaccca agttcatggt aaaggaacga atctgcttac agccattatc cattgtcccc aatgtggcgc
caagtcagtc aaaaaccca agtccatggc aaaggaacga atctgcttac agccattatt cactgtcccc aatgtggcgc
caagtcagtc aaaaaccca agtccatggc aaaggaacga atctgcttac agccattatt cactgtcccc aatgtggcgc
caagtcagtc aaaaaccca agtccatggc aaaggaacga atctgcttac agccattatt cactgtcccc aatgtggcgc <<<<<<<<<<ccrAB-R4<<<<<<
acctatggca gcaagcaata caacgaatac acttaaagat gggaccaaga aacgtattcg ttactattca tgtagtaatt
acctatggca gcaagcaata ccacgaatac tcttaaagac gggactaaga aacgtattcg ttactattca tgtagtaatt
acctatggca gcaagcaata ccacgaatac acttaaagac gggactaaga aacgtattcg ttactattca tgtagtaatt
acctatggca gcaagcaata ccacgaatac acttaaagac gggactaaga aacgtattcg ttactattca tgtagtaatt <<<<<<<<<<<ccrAB-R5<<<<<<<<<<
ttcggaacaa gggttccaaa gtatgttcgg caaac 2501bp
ttcggaacaa gggttccaaa gtatgttcgg caaac 2501bp
ttcggaacaa gggttccaaa gtatgttcgg caaac 2501bp
ttcggaacaa gggttccaaa gtatgttcgg caaac 2501bp
```

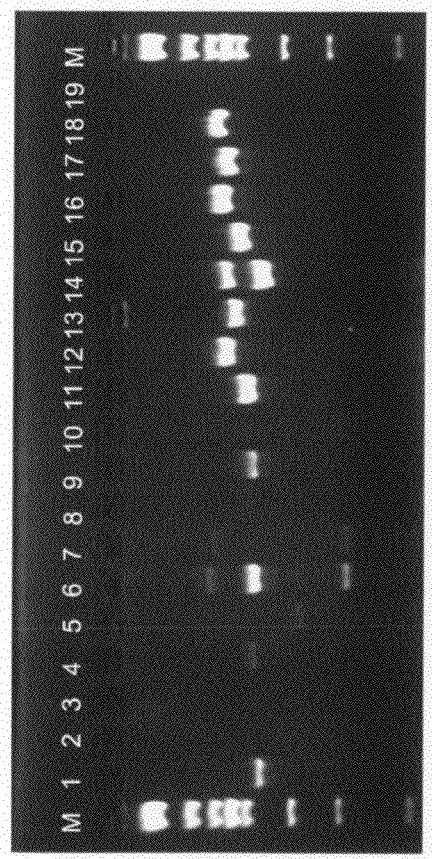

FIG. 17

| Lane | Strain | Predicted Results | Results |
|---|---|---|---|
| M = molecular weight marker | | | |
| 1 to 10 = MRSA negative patient samples | | negative | background amplification with human DNA. |
| 11 = MRSA SCC Type I | (ATCC BAA-38) | 566 bp amplicon | amplification |
| 12 = MRSA SCC Type II | (Microbiologics 0158p) | 668 bp amplicon | amplification |
| 13 = MRSA SCC Type III | (ATCC BAA-39) | 622 bp amplicon | amplification |
| 14 = MRSA SCC Type IV | (ATCC BAA-1556) | 668 bp amplicon | amplification |
| 15 = SCC mec I plasmid control | | 507 bp amplicon | amplification |
| 16 = SCC mec II plasmid control | | 566 bp amplicon | amplification |
| 17 = SCC mec III plasmid control | | 668 bp amplicon | amplification |
| 18 = SCC mec IV plasmid control | | 622 bp amplicon | amplification |
| 19 = No Template Control | | 668 bp amplicon | amplification |
| | | Negative control | negative |

FIG. 19

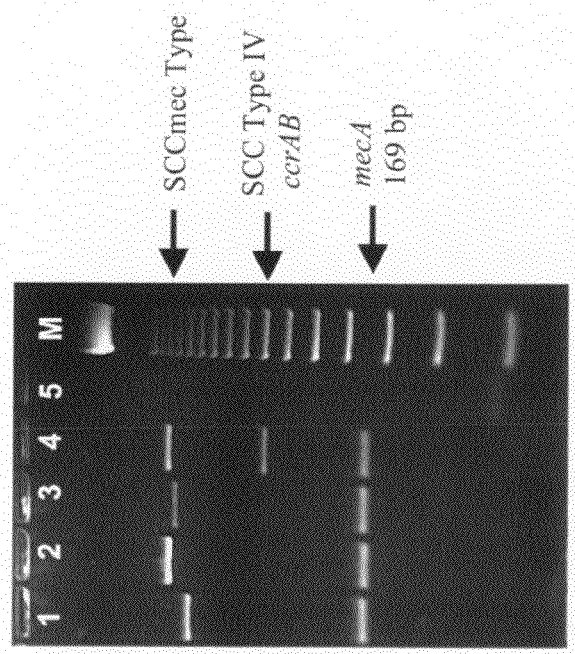

| Lane | Strain | Predicted Results | Results |
|---|---|---|---|
| 1 = MRSA SCC Type I | (ATCC BAA-38) | 566 bp amplicon<br>169 bp amplicon | amplification<br>amplification |
| 2 = MRSA SCC Type II | (Microbiologics 0158p) | 668 bp amplicon<br>169 bp amplicon | amplification<br>amplification |
| 3 = MRSA SCC Type III | (ATCC BAA-39) | 622 bp amplicon<br>169 bp amplicon | amplification<br>amplification |
| 4 = MRSA SCC Type IV | (ATCC BAA-1556) | 668 bp amplicon<br>334 bp amplicon<br>169 bp amplicon | amplification<br>amplification<br>amplification |
| 5 = No Template Control | | Negative control | negative |
| M = molecular weight marker | | | |

Arrows indicate: SCCmec Type, SCC Type IV ccrAB, mecA 169 bp

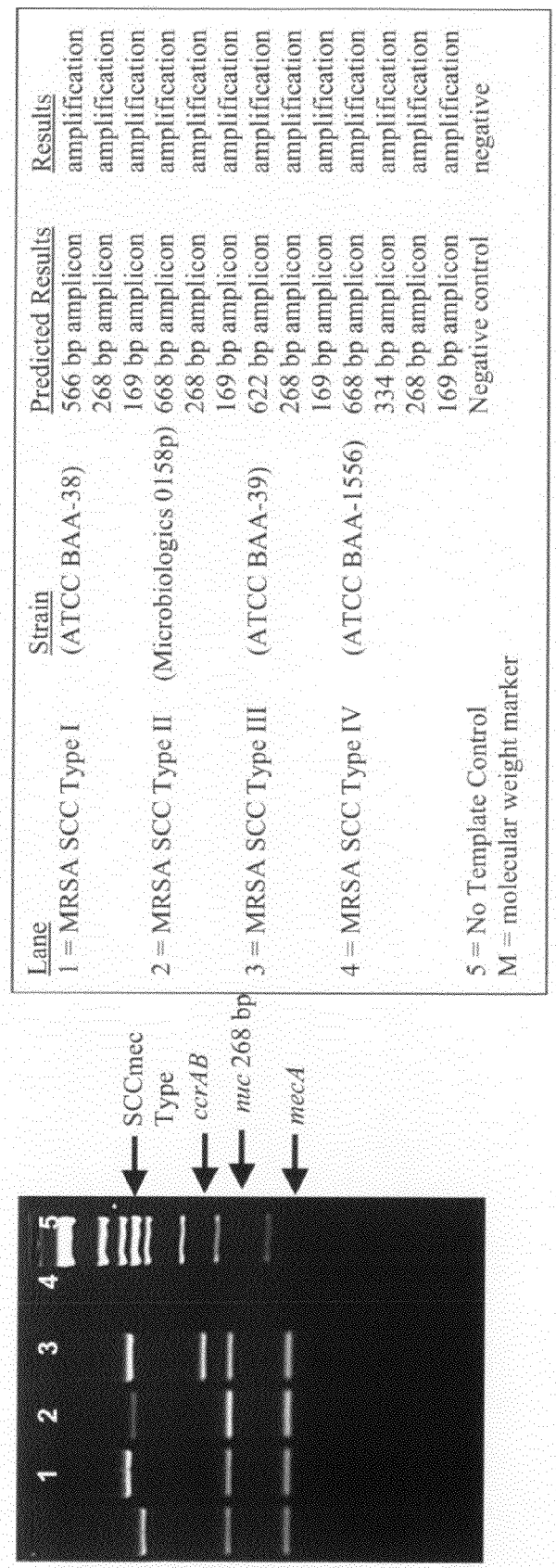

Standard curve of PVL real-time PCR.

SEQUENCE LISTING

```
<160> NUMBER OF SEQ ID NOS: 40

<210> SEQ ID NO 1
<211> LENGTH: 29
<212> TYPE: DNA
<213> ORGANISM: Staphylococcus aureus

<400> SEQUENCE: 1
gttgataaca atttggagga ccaaacgac                                      29

<210> SEQ ID NO 2
<211> LENGTH: 24
<212> TYPE: DNA
<213> ORGANISM: Staphylococcus aureus

<400> SEQUENCE: 2
gataacaatt tggaggacca aacg                                           24

<210> SEQ ID NO 3
<211> LENGTH: 22
<212> TYPE: DNA
<213> ORGANISM: Staphylococcus aureus
```

<400> SEQUENCE: 3
cttgtggata actggaaagt tg                                    22

<210> SEQ ID NO 4
<211> LENGTH: 20
<212> TYPE: DNA
<213> ORGANISM: Staphylococcus aureus

<400> SEQUENCE: 4
gagggaacag tgtgaacaag                                       20

<210> SEQ ID NO 5
<211> LENGTH: 27
<212> TYPE: DNA
<213> ORGANISM: Staphylococcus aureus

<400> SEQUENCE: 5
cactaaaaat cgggcataaa tgtcagg                               27

<210> SEQ ID NO 6
<211> LENGTH: 26
<212> TYPE: DNA
<213> ORGANISM: Staphylococcus aureus

<400> SEQUENCE: 6
cgactgtacg acgtagaaaa gctagc                                26

<210> SEQ ID NO 7
<211> LENGTH: 29
<212> TYPE: DNA
<213> ORGANISM: Staphylococcus aureus

<400> SEQUENCE: 7
gtcaaaaatc atgaacctca ttacttatg                             29

<210> SEQ ID NO 8
<211> LENGTH: 22
<212> TYPE: DNA
<213> ORGANISM: Staphylococcus aureus

<400> SEQUENCE: 8
gactgcggag gctaactatg tc                                    22

<210> SEQ ID NO 9
<211> LENGTH: 27
<212> TYPE: DNA
<213> ORGANISM: Staphylococcus aureus

<400> SEQUENCE: 9
gaactttgct tcactataag tattcag                               27

<210> SEQ ID NO 10
<211> LENGTH: 29
<212> TYPE: DNA
<213> ORGANISM: Staphylococcus aureus

<400> SEQUENCE: 10
atttcatata tgtaattcct ccacatctc                             29

<210> SEQ ID NO 11
<211> LENGTH: 25
<212> TYPE: DNA
<213> ORGANISM: Staphylococcus aureus

```
<400> SEQUENCE: 11
cgtatgatat tgcaaggtat aatcc                                              25

<210> SEQ ID NO 12
<211> LENGTH: 24
<212> TYPE: DNA
<213> ORGANISM: Staphylococcus aureus

<400> SEQUENCE: 12 gcttttcca ctcccatttc ttcc                                                24

<210> SEQ ID NO 13
<211> LENGTH: 21
<212> TYPE: DNA
<213> ORGANISM: Staphylococcus aureus

<400> SEQUENCE: 13
ctagtcttct taaccattca c                                                  21

<210> SEQ ID NO 14
<211> LENGTH: 23
<212> TYPE: DNA
<213> ORGANISM: Staphylococcus aureus

<400> SEQUENCE: 14
gttgaaagat gcaaaagaag gca                                                23

<210> SEQ ID NO 15
<211> LENGTH: 22
<212> TYPE: DNA
<213> ORGANISM: Staphylococcus aureus

<400> SEQUENCE: 15
cagacctgag ctccaacgta tg                                                 22

<210> SEQ ID NO 16
<211> LENGTH: 24
<212> TYPE: DNA
<213> ORGANISM: Staphylococcus aureus

<400> SEQUENCE: 16
cgtggtattt caggtaaatc tatg                                               24

<210> SEQ ID NO 17
<211> LENGTH: 24
<212> TYPE: DNA
<213> ORGANISM: Staphylococcus aureus

<400> SEQUENCE: 17
gtatctatgt acgtgtatca acag                                               24

<210> SEQ ID NO 18
<211> LENGTH: 27
<212> TYPE: DNA
<213> ORGANISM: Staphylococcus aureus

<400> SEQUENCE: 18
gttaatcatt agctcctgtt tactatc                                            27

<210> SEQ ID NO 19
<211> LENGTH: 21
<212> TYPE: DNA
<213> ORGANISM: Staphylococcus aureus
```

-continued

<400> SEQUENCE: 19
gtgacatatc ctttgtgatt c                                              21

<210> SEQ ID NO 20
<211> LENGTH: 23
<212> TYPE: DNA
<213> ORGANISM: Staphylococcus aureus

<400> SEQUENCE: 20
caaattgaat tttgccgata tag                                            23

<210> SEQ ID NO 21
<211> LENGTH: 28
<212> TYPE: DNA
<213> ORGANISM: Staphylococcus aureus

<400> SEQUENCE: 21
agatagtaaa cacgagctaa tgattaac                                       28

<210> SEQ ID NO 22
<211> LENGTH: 22
<212> TYPE: DNA
<213> ORGANISM: Staphylococcus aureus

<400> SEQUENCE: 22
ctacatgaat agtaacgaat ac                                             22

<210> SEQ ID NO 23
<211> LENGTH: 29
<212> TYPE: DNA
<213> ORGANISM: Staphylococcus aureus

<400> SEQUENCE: 23
gccgaacata ctttggaacc cttgttccg                                      29

<210> SEQ ID NO 24
<211> LENGTH: 24
<212> TYPE: DNA
<213> ORGANISM: Staphylococcus aureus

<400> SEQUENCE: 24
gtactgctat ccaccctcaa acag                                           24

<210> SEQ ID NO 25
<211> LENGTH: 24
<212> TYPE: DNA
<213> ORGANISM: Staphylococcus aureus

<400> SEQUENCE: 25
gaacctggtg aagttgtaat ctgg                                           24

<210> SEQ ID NO 26
<211> LENGTH: 18
<212> TYPE: DNA
<213> ORGANISM: Staphylococcus aureus

<400> SEQUENCE: 26
gtgctggcat atgtatgg                                                  18

<210> SEQ ID NO 27
<211> LENGTH: 21
<212> TYPE: DNA
<213> ORGANISM: Staphylococcus aureus

<400> SEQUENCE: 27
cgctttaatt aatgtcgcag g                                      21

<210> SEQ ID NO 28
<211> LENGTH: 25
<212> TYPE: DNA
<213> ORGANISM: Staphylococcus aureus

<400> SEQUENCE: 28
agtcaaatca tcagttgtta catca                                  25

<210> SEQ ID NO 29
<211> LENGTH: 20
<212> TYPE: DNA
<213> ORGANISM: Staphylococcus aureus

<400> SEQUENCE: 29
atcggaatct gatgttgcag                                        20

<210> SEQ ID NO 30
<211> LENGTH: 26
<212> TYPE: DNA
<213> ORGANISM: Staphylococcus aureus

<400> SEQUENCE: 30
atgcagctca acatatcaca cctgta                                 26

<210> SEQ ID NO 31
<211> LENGTH: 1491
<212> TYPE: DNA
<213> ORGANISM: Staphylococcus aureus

<400> SEQUENCE: 31
caaagttcaa gcccagaagc gatgtttgta ttattagcag gtataggttt aatcgcgact    60
gtacgacgta gaaaagctag ctaaaatata ttgaaaataa tactactgta tttcttaaat   120
aagaggtacg gtagtgtttt tttatgaaaa aaagcgataa ccgttgataa atatgggata   180
taaaaacgag gataagtaat aagacatcaa ggtgtttatc cacagaaatg gggatagtta   240
tccagaattg tgtacaattt aaagagaaat acccacaatg cccacagagt tatccacaaa   300
tacacaggtt atacactaaa aatcgggcat aaatgtcagg aaaatatcaa aaactgcaaa   360
aaatattggt ataataagag ggaacagtgt gaacaagtta ataacttgtg gataactgga   420
aagttgataa caatttggag gaccaaacga catgaaaatc accattttag ctgtagggaa   480
actaaaagag aaatattgga agcaagccat agcagaatat gaaaaacgtt taggcccata   540
caccaagata gacatcatag aagttccaga cgaaaaagca ccagaaaata tgagtgacaa   600
agaaattgag caagtaaaag aaaaagaagg ccaacgaata ctagccaaaa tcaaaccaca   660
atccacagtc attacattag aaatacaagg aaagatgcta tcttccgaag gattggccca   720
agaattgaac caacgcatga cccaagggca aagcgacttt gttttcgtca ttggcggatc   780
aaacggcctg cacaaggacg tcttacaacg cagtaactac gcactatcat tcagcaaaat   840
gacattccca catcaaatga tgcgggttgt gttaattgaa caagtgtaca gagcatttaa   900
gattatgcga ggagaggcgt atcataagta aaatttggag ggtgttaaat ggtggacatt   960
aaatccacgt tcattcaata tataagatat atcacgataa ttgcgcatat aacttaagta  1020
gtagctaaca gttgaaatta ggccctatca aattggttta tatctaaaat gattaatata  1080
gaatgcttct ttttgtcctt attaaattat aaaagtaact ttgcaataga aacagttatt  1140

```
tcataatcaa cagtcattga cgtagctaag taatgataaa taatcataaa taaaattaca    1200
gatattgaca aaaatagta aatataccaa tgaagtttca aaagaacaat tccaagaaat    1260
tgagaatgta ataataagg tcaaagaatt ttattaagat ttgaaagagt atcaatcaag    1320
aaagatgtag ttttttaata aactatttgg aaaataatta tcataattta aaaactgaca    1380
atttgcgaga ctcataaaat gtaataatgg aaatagatgt aaaatataat taagggtgt    1440 aatatgaaga ttaatattta taaatctatt tataattttc aggaaacaaa t             1491
```

<210> SEQ ID NO 32
<211> LENGTH: 500
<212> TYPE: DNA
<213> ORGANISM: Staphylococcus aureus

<400> SEQUENCE: 32

```
accaaataat atccatcctt tgtttctttt gttatattct catcatatat tgaaatccaa     60
ggaactttac tatagttccc agtagcaacc ttccctacaa ctgaatattt atcttctttt    120
atatgcactt ttaactgctt gggtaactta tcatggacta agttttata tagatcacct    180 ttatcccaat cagattttt aactacatta ttggtacgtt tctctttaat taatttaagg    240
acctgcataa agttgtctat catttgaaat tccctcctat tataaaatat attatgtctc    300
attttcttca atatgtactt atttatattt taccgtaatt tactatattt agttgcagaa    360
agaattttct caaagctaga actttgcttc actataagta ttcagtataa agaatatttc    420
gctattattt acttgaaatg aaagactgcg gaggctaact atgtcaaaaa tcatgaacct    480
cattacttat gataagcttc                                                500
```

<210> SEQ ID NO 33
<211> LENGTH: 500
<212> TYPE: DNA
<213> ORGANISM: Staphylococcus aureus

<400> SEQUENCE: 33

```
gaatatttat cttctttat atgcactttt aactgcttgg gtaacttatc atggactaaa     60
gttttatata gatcaccttt atcccaatca gattttttaa ctacattatt ggtacgtttc    120
tctttaatta atttaaggac ctgcataaag ttgtctatca tttgaaattc cctcctatta    180 taaatatat tatgtctcat tttcttcaat atgtacttat ttatatttta ccgtaattta    240
ctatatttag ttgcagaaag aattttctca aagctagaac tttgcttcac tataagtatt    300
cagtataaag aatatttcgc tattatttac ttgaaatgaa agactgcgga ggctaactat    360
gtcaaaaatc atgaacctca ttacttatga taagcttctt aaaaacataa cagcaattca    420 cataaaccte atatgttctg atacattcaa aatccccttta tgaagcggct gaaaaaaccg    480
catcatttat gatatgcttc                                                500
```

<210> SEQ ID NO 34
<211> LENGTH: 500
<212> TYPE: DNA
<213> ORGANISM: Staphylococcus aureus

<400> SEQUENCE: 34

```
aaatcaaaaa taacatacct tacaactttt accgtcgata tcaattgctc ttttcttaat     60
ttaggattgc tttcaaattt tgtactataa cgtgaaacta cttttccttc tttataatta    120
aaatttacta attcacaatc attttttactt ccatttacaa aaacatccac tgtttctaac    180
acaaaatcta ataaacttcc ttttattaat cgtaggcatt gtatatttcc tttcattctt    240
```

```
tcttgattcc attagtttaa atttaaaatt tcatccatca atttcttaat ttaattgtag    300
ttccataatc aatataattt gtacagttat tatatattct agatcatcaa tagttgaaaa    360
atggtttatt aaacactcta taaacatcgt atgatattgc aaggtataat ccaatatttc    420
atatatgtaa ttcctccaca tctcattaaa tttttaaatt atacacaacc taatttttag    480
ttttatttat gatacgcttc                                                500

<210> SEQ ID NO 35
<211> LENGTH: 500
<212> TYPE: DNA
<213> ORGANISM: Staphylococcus aureus

<400> SEQUENCE: 35
gaatatttat cttcttttat atgcactttt aactgcttgg gtaacttatc atggactaaa     60
gttttatata gatcaccttt atcccaatca gatttttaa ctacattatt ggtacgtttc    120
tctttaatta atttaaggac ctgcataaag ttgtctatca tttgaaattc cctcctatta    180
taaaatatat tatgtctcat tttcttcaat atgtacttat ttatatttta ccgtaattta    240
ctatatttag ttgcagaaag aatttttctca agctagaac tttgcttcac tataagtatt    300
cagtataaag aatatttcgc tattatttac ttgaaatgaa agactgcgga ggctaactat    360
gtcaaaaatc atgaacctca ttacttatga taagcttctt aaaaacataa cagcaattca    420
cataaacctc atatgttctg atacattcaa aatcccttta tgaagcggct gaaaaaaccg    480
catcatttat gatatgcttc                                                500

<210> SEQ ID NO 36
<211> LENGTH: 500
<212> TYPE: DNA
<213> ORGANISM: Staphylococcus aureus

<400> SEQUENCE: 36
ataaaaagca ttaactggat cttgtcagc attcctcttc tgcttaacca cattactacc     60
tatttcaaat ctttctctag cttcatttag tctgatattc attttattgt aaattctttc    120
ttttgaatgc ttaagttcac tattttccg agtaataaaa ttttctaaac tatttatagc    180
gctatttaaa tgcttaattt ggtcactatg atttatagat tcttctccaa taaccaaatt    240
cacaccatct atttcttcaa cttcttcaat attattttt aagtaaccag tattaaagat    300 aacactttt tcattatcta gtcttcttaa ccattcactt aatgagcttt ttccactccc    360
atttcttcca aaaatatat ttactttagt caaatcatct tcactagtgt aattatcgaa    420
tgatttataa ctaacatttt ctaatttatt taacataaaa tcaatccttt ttatatttaa    480
aatatattat acacaatccg                                                500

<210> SEQ ID NO 37
<211> LENGTH: 1055
<212> TYPE: DNA
<213> ORGANISM: Staphylococcus aureus

<400> SEQUENCE: 37
tgaagaaagg atgtaacata atgcaacaac ttaaaacaaa acgtgtcggt atctatgtac     60
gtgtatcaac agaaatgcaa agcacagaag gttatagtat cgacggacaa atcaatcaaa    120
tcaaagaata ctgtgacttc catcatttg aagttaaaga tatatacgct gatcgtggta    180
tttcaggtaa atctatgaac agacctgagc tccaacgtat gttgaaagat gcaaaagaag    240
gcaatataga ttgtgttatg atctacaaaa caaaccgatt agctcgtaat acatcggatc    300
```

```
ttctgaaaat cgtcgaagat ttgcataaac aaaatgtcga attttcagt ttatcagagc    360 gtatggaagt caatacttct tctggtaaac tcatgttaca atacttgcg agtttctcag    420 aattcgaacg taataacatt gtcgagaatg tatttatggg gcaaacgaga cgtgcccaag    480
aaggctatta tcaaggcaat ttaccactag gttatgacaa ataccagat agtaaacacg    540 agctaatgat taaccaacat gaagctaata ttgtaaaata tatattcgag tcctatgcca    600
aaggacatgg ctatcgtaaa atagccaatg cattgaatca caaggctat gtcactaaaa    660 agggtaaacc ttttagtatt agttctatca catatatatt agctaaccca ttctatatcg    720
gcaaaattca atttgcgaaa tacaaagatt ggagtgaaaa acgtcgtaaa gggctgaatg    780
ataaaccagt gatagctgaa ggtaagcatt ccccccattat taatcaagat ttatgggata    840
aagtacaaat gcgtaaaaaa caagtcagtc aaaaacccca agttcatggt aaaggaacga    900
atctgcttac aggcattatc cattgtcccc aatgtggcgc acctatggca gcaagcaata    960
caacgaatac acttaaagat gggaccaaga aacgtattcg ttactattca tgtagtaatt   1020
ttcggaacaa gggttccaaa gtatgttcgg caaac                              1055
```

<210> SEQ ID NO 38
<211> LENGTH: 1055
<212> TYPE: DNA
<213> ORGANISM: Staphylococcus aureus

<400> SEQUENCE: 38

```
tgaagaaagg atgtaacata atgcaacaac ttaaaacaaa acgtgtcggt atctatgtac     60
gtgtatcaac agaaatgcaa agcacagaag gttatagtat cgacggacaa atcaatcaaa    120
tcaaagaata ctgtgacttc catcattttg aagttaaaga tatatacgct gaccgtggta    180
tttcaggtaa atctatgaac agacctgagc tccaacgtat gttgaaagat gcaaaagaag    240
gcaatatcga ctgtgttatg gtatacaaaa caaaccgatt agctcgtaat acatctgatc    300
ttctcaaaat tgtcgaagat ttacacaaac aaaatgtcga attttcagt ttgtcagagc    360 gtatggaagt caatacttct tctggtaaac tcatgttaca gatacttgcg agtttctcag    420
aattcgaacg taataacatt gtcgagaacg tatttatggg tcaaacgaga cgtgcccaag    480
aaggctatta tcaaggcaat ttaccactag gttatgacaa ataccagat agtaaacacg    540 agctaatgat taaccaacat gaagctaata ttgtaaaata tatattcgag tgctatgcca    600
aaggacatgg ctatcgtaaa attgccaatg cattgaatca caaggatat gtcactaaaa    660 agggggaaacc tttcagtatt agttcaatca catacatctt agctaaccct ttctatatcg    720
gcaaaattca atttgcgaaa tacaaagatt ggagtgaaaa acgtcgtaaa gggctgaatg    780
ataaaccagt gatagctgaa ggtaagcatt ccccccattat taatcaagat ttatgggata    840
aagtacaaat gcgtaagaaa caagtcagtc aaaaacccca agtccatggc aaaggaacga    900
atctgcttac aggcattatt cactgtcccc aatgtggcgc acctatggca gcaagcaata    960
ccacgaatac tcttaaagac gggactaaga aacgtattcg ttactattca tgtagtaatt   1020
ttcggaacaa gggttccaaa gtatgttcgg caaac                              1055
```

<210> SEQ ID NO 39
<211> LENGTH: 1055
<212> TYPE: DNA
<213> ORGANISM: Staphylococcus aureus

<400> SEQUENCE: 39

```
cgaagaaagg atgaaacata atgcaacaac ttaaaacaaa acgtgtcggt atctatgtac     60
```

```
gtgtatcaac agaaatgcaa agcacagaag gttatagtat cgacggacaa atcaatcaaa    120
tcaaagaata ctgtgacttc catcattttg aagttaaaga tatatacgct gaccgtggta    180
tttcaggtaa atctatgaat cgacctgagc tccaacgtat attgaaggat gcgaaagaag    240
gctatatcga ctgtgttatg gtctacaaaa caaaccgatt agctcgtaat acatctgatc    300
ttctcaaaat tgtcgaagat ttacacaaac aaaatgtcga atttttcagt ttatcagagc    360
gtatggaagt caatacttca tcgggtaagc tcatgttaca aatacttgcg agtttctcag    420
aattcgaacg taataacatt gtcgagaatg tatttatggg tcaaacgaga cgtgcccaag    480
aaggctatta tcaaggcaat ttgccgctgg gctatgacaa atacctaat agtaaacatg     540 aactgatgat taatcaacat gaagctaata ttgtgaaata tatattcgag tcctatgcca    600
aaggccatgg ctatcgtaaa atagccaatg cattaaatca caaaggctat gtcactaaaa    660
agggtaaacc ttttagtatt agttctatca catatatatt agctaaccca ttctatatcg    720
gcaaaattca atttgcgaaa tacaaagatt ggagtgaaaa acgtcgtaaa gggcttaatg    780
ataaaccagt gatagctgaa ggtaagcatt cccccattat taatcaagat ttatgggata    840
aagtacaaat gcgtaaaaaa caagtcagtc aaaaacccca agtccatggc aaaggaacga    900
atctgcttac aggcattatt cactgtcccc aatgtggcgc acctatggca gcaagcaata    960
ccacgaatac acttaaagac gggactaaga aacgtattcg ttactattca tgtagtaatt   1020
ttcggaacaa gggttccaaa gtatgttcgg caaac                              1055

<210> SEQ ID NO 40
<211> LENGTH: 1055
<212> TYPE: DNA
<213> ORGANISM: Staphylococcus aureus

<400> SEQUENCE: 40
cgaagaaagg atgaaacata atgcaacaac ttaaaacaaa acgtgtcggt atctatgtac     60
gtgtatcaac agaaatgcaa agcacagaag gttatagtat cgacggacaa atcaatcaaa    120
tcaaagaata ctgtgacttc catcattttg aagttaaaga tatatacgct gaccgtggta    180
tttcaggtaa atctatgaat cgacctgagc tccaacgtat attgaaggat gcgaaagaag    240
gctatatcga ctgtgttatg gtctacaaaa caaaccgatt agctcgtaat acatctgatc    300
ttctcaaaat tgtcgaagat ttacacaaac aaaatgtcga atttttcagt ttatcagagc    360
gtatggaagt caatacttca tcgggtaagc tcatgttaca aatacttgcg agtttctcag    420
aattcgaacg taataacatt gtcgagaatg tatttatggg tcaaacgaga cgtgcccaag    480
aaggctatta tcaaggcaat ttgccgctgg gctatgacaa atacctaat agtaaacatg     540 aactgatgat taatcaacat gaagctaata ttgtgaaata tatattcgag tcctatgcca    600
aaggccatgg ctatcgtaaa atagccaatg cattaaatca caaaggctat gtcactaaaa    660
agggtaaacc ttttagtatt agttctatca catatatatt agctaaccca ttctatatcg    720
gcaaaattca atttgcgaaa tacaaagatt ggagtgaaaa acgtcgtaaa gggcttaatg    780
ataaaccagt gatagctgaa ggtaagcatt cccccatttt taatcaagat ttatgggata    840
aagtacaaat gcgtaaaaaa caagtcagtc aaaaacccca agtccatggc aaaggaacga    900
atctgcttac aggcattatt cactgtcccc aatgtggcgc acctatggca gcaagcaata    960
ccacgaatac acttaaagac gggactaaga aacgtattcg ttactattca tgtagtaatt   1020
ttcggaacaa gggttccaaa gtatgttcgg caaac                              1055
```

METHOD OF DETERMINING TYPES I, II, III, IV OR V OR METHICILLIN-RESISTANT *STAPHYLOCOCCUS AUREUS* (MRSA) IN A BIOLOGICAL SAMPLE

CROSS-REFERENCE TO RELATED APPLICATION

The present application claims the benefit of priority under 35 U.S.C. §119(e) to U.S. Provisional Application No. 61/335,874 filed Jan. 13, 2010, the entire disclosure of which is hereby incorporated by reference in its entirety.

FIELD OF THE INVENTION

Example embodiments are generally directed to methods of determining types I, II, III, IV or V of methicillin-resistant *Staphylococcus aureus* (MRSA) in a biological sample of a mammal, such as a human. More specifically, example embodiments include a multiplex PCR assay where pairs of primers are used to differentiate types I, II, III, IV or V in a single PCR reaction without the burden of performing cell culturing. Additional embodiments are directed to methods for screening for MRSA; methods of treatment; kits for determining MRSA types in a mammal; and isolated primers that may be used in the present methods and kits.

BACKGROUND OF THE INVENTION

Methicillin-resistant *Staphylococcus aureus* (MRSA) is a *Staphylococcus aureus* variant containing a Staphylococcal Chromosome Cassette (SCC) transposon that has been integrated into the genome of *Staphylococcus aureus*. There are at least five (5) types of MRSA; namely types I, II, III, IV and V. Types I-III are the hospital associated MRSA (HA-MRSA), with type II being the most prevalent among the HA-MRSA. Types IV-V, together with their expression of the Panton-Valentine Leukocidin (PVL) toxin, represent the community associated-MRSA (CA-MRSA). SCC in HA-MRSA is a larger mobile genetic element (when compared to CA-MRSA) that can incorporate many antibiotic resistance genes against clindamycin or doxycyline. However, CA-MRSA is more virulent than HA-MRSA. MRSA identification and SCC typing are crucial for medical diagnosis. An accurate and speedy assay to identify MRSA and its SCC types at the early stage of bacterial infection is urgently needed, so as to provide an adequate time window for proper antibiotics treatment to save human lives.

SCC integrates into the *Staphylococcus aureus* genome at a specific site within the orfX gene. The SCC contains numerous genes including, for example, mecA, mecR, mecI, and ccrAB. The mecA gene encodes an alternative penicillin binding protein 2 (PBP2a) that exhibits a lower affinity towards β-lactam antibiotics. The mecR gene encodes a receptor for β-lactam antibiotics, and the mecI gene encodes a transcriptional repressor for the mecA gene. Altogether, the mecA, mecR, and mecI account for the methicllin resistance for *Staphylococcus aureus*. The ccrAB gene is required for the transposition of the SCC mobile element.

Presently, commercial detection of MRSA involves cell culturing followed by molecular PCR technology. Specifically, *Staphylococcus*-containing micro-organisms are plated onto Staphylococcal selective and differential media such as Manitol Salt Agar with phenol red or Staphylococcal CHRO-MAgar. This cell culture procedure allows the selection of *Staphylococcus aureus*.

After the culture plating, *Staphylococcus aureus* DNA is isolated and subjected to PCR assay for the presence of the mecA gene. mecA gene is known to exist in the SCC of MRSA, but not in methicillin-susceptible *Staphylococcus aureus* (MSSA). Thus, detection of the mecA gene in the chromosomal DNA of *Staphylococcus aureus* by PCR or hybridization makes it possible to differentiate MRSA from MSSA. Unfortunately, detection of mecA is not specific for *Staphylococcus aureus*, because other *Staphylococcus* spp. may contain SCC that contains mecA. Such *Staphylococcus* spp. include, for example, coagulase-negative *Staphylococcus*.

Other alternative means for detecting MRSA involves PCR amplification of the 5' orfX mecDNA junction. However, mecA gene may loop out from the SCC by gene recombination. When this occurs, false positive results would ensure from the PCR amplification test. U.S. Pat. No. 6,156,507 discloses use of single-pair primers, with the forward exclusively within orf X (IntM) and the reverse within the mecA region. Because SCCmec transposon can pop out from the *Staphylococcus aureus*, leaving behind a portion of the right extremity (RE) region, this assay is not ideal because it often yields false-positive result. U.S. Pat. No. 2008/0220428 discloses a real-time PCR utilizing multiple primer pairs specifically targeting within orf X and mecA region and the RE region of SCCmec. This assay also yields false-positive results for the same reason.

U.S. Pat. Nos. 2007/0082340, 2008/0227087 and 2006/0252078 similarly disclose use of single-pair primers that target the SCCmec right extremity junction (MREJ) in a PCR reaction. These authors stated their tests are capable of distinguishing twenty (20) MRSA subtypes (i.e., Types I to XX). The '340 and '087 applications specifically target within SCCmec region (i.e., mecA), while '078 application targets regions extended to IntM region as well as 5' UTR.

U.S. Pat. No. 2006/0252069 discloses a multiplex PCR assay using ccrAB primers. Because SCCmec transposon can exist in *Staphylococcus aureu* and non-*Staphylococcus aureu* bacteria (i.e., SCCmec transposon can insert into coagulase-negative *Staphylococcus* spp.). The '069 method cannot distinguish *Staphylococcus aureus* from these coagulase-negative staphylococci. A separate test (i.e., cell culture and isolation) is required for determining *Staphylococcus aureus* identity.

Commercial detection of MRSA involves first identification of MRSA, followed by the SCC typing. With respect to SCC typing, PCR amplification of the hypervariable regions of the ccrAB gene sequence provides useful information in differentiating types I-V. SCC typing may also be performed by PCR amplification at the left arm of the 5' orfX mecDNA junction. The major disadvantage of these procedures relates to the fact that they take a minimal time period of 24-48 hours. Because physicians are reluctant to provide any empiric therapy until the MRSA SCC typing is identified, these assays involving ccrAB gene and 5' orfX mecDNA junction are not ideal.

Current methods for distinguishing CA-MRSA from HA-MRSA involve identifying the Staphylococcal Chromosomal Cassette (SCC) mec element, together with the PVL toxin. Hence, CA-MRSA contains a SCCMec type IV cassette and possesses the PVL toxin. In contrast, HA-MRSA contains SCCMec type I-III but lacks PVL toxin. Unfortunately, MRSA PCR assays are unduly complicated. First, one must use multiple oligonucleotide primers to verify: (i) if the isolate is *Staphylococcus aureus*; (ii) if the isolate contains a mecA gene; and (iii) if the isolate contains a SCC Mec I-IV typing. After this PCR determination, a second PCR reaction must then be performed to show the presence or absence of PVL toxin. Because these are two separate PCR reactions, and involves the use of multiple primers and probes in respective PCR reactions, the entire procedure is both time-consuming and expensive. Such assay is overly complicated and causes delay in the diagnosis of MRSA.

A further method for determining CA-MRSA is multilocus sequence typing (MLST). In MLST, a number of housekeeping genes are sequenced and compared to reference strains. Pulsed-field gel electrophoresis (PFGE) is also used in which digested genomic DNA is separated across an agarose gel in several different orientations to gain resolution of large bands of DNA. Both MLST and PFGE are time-consuming and require a high degree of skill in order to successfully interpret results, making them less than optimal for use in medical diagnostics.

All these prior art methodologies suffer either suboptimal specificity or unacceptable long assay time. Accordingly, there is a continuing need for an accurate, rapid and simple PCR assay to detect MRSA and simultaneously determine its SCC types (i.e., types I, II, III, IV or V), preferably in a single PCR reaction.

SUMMARY OF THE INVENTION

Example embodiments are directed to diagnostic methods of determining a subtype of methicillin-resistant *Staphylococcus aureus* (MRSA) in a biological sample of a mammal, such as a human. Methods include providing a biological sample of the mammal, performing a PCR analysis of the biological sample, and analyzing the PCR amplicons with respect to their sizes so as to determine for type I, type II, type III or type IV MRSA that are present in the biological sample. The PCR analysis may provide determination for type IV MRSA as well.

The PCR analysis includes the use of *Staphylococcus aureus* species-specific primers. Specifically, a forward primer is located in the 5' UTR, and reverse primers are located with the SCCmec DNA downstream of the 5' orfX-mecDNA junction (See, FIG. 1). This unique design of multiple primer pairs offer *Staphylococcus aureus* species-specificity as well as discrimination for type I, II/IV and III. Distinction between type II from type IV comes from SCC-mec Type IV specific primers targeted against the ccrAB genes. Together, the present invention provides novel primer pairs that are useful in a multiplex PCR reaction and allows specific determination of type IV MRSA and confirmation of *Staphylococcus aureus*, all in a single PCR reaction.

Further example embodiments include using at least one mecA primer pair and/or using at least one *Staphylococcus aureus* nuc primer pair in the PCR analysis.

Additional embodiments are directed to methods for screening populations to determine a subtype of MRSA in individuals of the population. For example, pre-screening patients upon admission to a medical facility for MRSA may allow facilities to care for patients accordingly. To be effective in preventing MRSA infection, hospitals and healthcare facilities need to correctly sanitize surface areas where patients have direct contact.

Example embodiments are also directed to methods of treating a mammal that include determining a subtype of MRSA in a biological sample and administering an effective amount of at least one non β-lactam antibiotics to a mammal testing positive for Type IV MRSA. Upon detection of MRSA, MRSA can be treated with appropriate alternate antibiotics, such as glycopeptides (vancomycin and teichoplanin), linizolid, and daptomycin.

Also provided are kits for determining a MRSA subtype in a mammal, which kits include *Staphylococcus aureus* specific primer pairs for detecting MRSA SCC Type, I, II, III and IV; and at least one SCCmec Type IV specific primer pair targeting the ccrAB genes.

Further provided are isolated primers that may be used in the present methods and kits.

BRIEF DESCRIPTION OF THE FIGURES

Embodiments of the invention are herein described, by way of non-limiting example, with reference to the following accompanying figures:

FIG. 2 depicts the nucleotide sequences for *Staphylococcus aureus* specific primers targeting the 5' UTR and 5' orf0022 of the Newman Genome sequence (NC009641). Newman genome sequence from 33241 to 34761 bp.

FIG. 3 depicts *Staphylococcus aureus* cassette chromosome (SCC) mec Type I.

FIG. 4 depicts *Staphylococcus aureus* cassette chromosome (SCC) mec Type II.

FIG. 5 depicts *Staphylococcus aureus* cassette chromosome (SCC) mec Type III.

FIG. 6 depicts *Staphylococcus aureus* cassette chromosome (SCC) mec Type IV.

FIG. 7 depicts *Staphylococcus aureus* cassette chromosome (SCC) mec Type V.

FIG. 8 depicts nucleotide sequence alignment of the 5' end of the SCCmec DNA from SCC types I, II, and IV located at the 5' orfX-mecDNA junction.

FIG. 9 depicts nucleotide sequence alignment of the 5' end of the SCCmec DNA from SCC types I, II, IV and III located at the 5' orfX-mecDNA junction.

FIG. 14 depicts nucleotide sequence alignment of the ccrAB gene.

FIG. 16 shows an SCC Typing multiplex PCR reaction with forward primer 5'UTR 3 (SEQ ID NO: 3) and reverse primers, mec124b (SEQ ID NO:8) and mec3b (SEQ ID NO:11) in combination with forward primer ccrAB-F2 (SEQ ID NO:15) and reverse primer ccrAB-R1 (SEQ ID NO:18).

FIG. 17 depicts multiplex PCR reactions using the ccrAB-F4 forward primer (SEQ ID NO:17) and the ccrAB-R1 reverse primer (SEQ ID NO:18). In particular, FIG. 17 shows an SCC Typing multiplex PCR reaction with forward primer 5'UTR 3 (SEQ ID NO: 3) and reverse primers, mec124b (SEQ ID NO:8) and mec3b (SEQ ID NO:11) in combination with forward primer ccrAB-F4 (SEQ ID NO:17) and reverse primer ccrAB-R1 (SEQ ID NO:18).

FIG. 18 shows an SCC Typing multiplex PCR reaction with forward primer 5'UTR 3 (SEQ ID NO: 3) and reverse primers, mec124b (SEQ ID NO:8) and mec3b (SEQ ID NO:11) in combination with forward primer ccrAB-F1 (SEQ ID NO:14) and reverse primer ccrAB-R1 (SEQ ID NO:18).

FIG. 19 depicts multiplex PCR reactions with the addition of mecA primers. In particular, FIG. 19 shows an SCC Typing multiplex PCR reaction with forward primer 5'UTR 3 (SEQ ID NO: 3) and reverse primers, mec124b (SEQ ID NO:8) and mec3b (SEQ ID NO:11) in combination with forward primer ccrAB-F1 (SEQ ID NO:14) and reverse primer ccrAB-R1 (SEQ ID NO:18), with the addition of the mecA forward and mecA reverse primers. The multiplex reactions successfully amplified and determined the SCCmec Types, the type IV specific ccrAB amplicon, and the presence of the mecA gene.

FIG. 20 depicts the multiplex PCR reactions with the addition of nuc primers.

DETAILED DESCRIPTION OF THE INVENTION

Definitions

Figure 1:
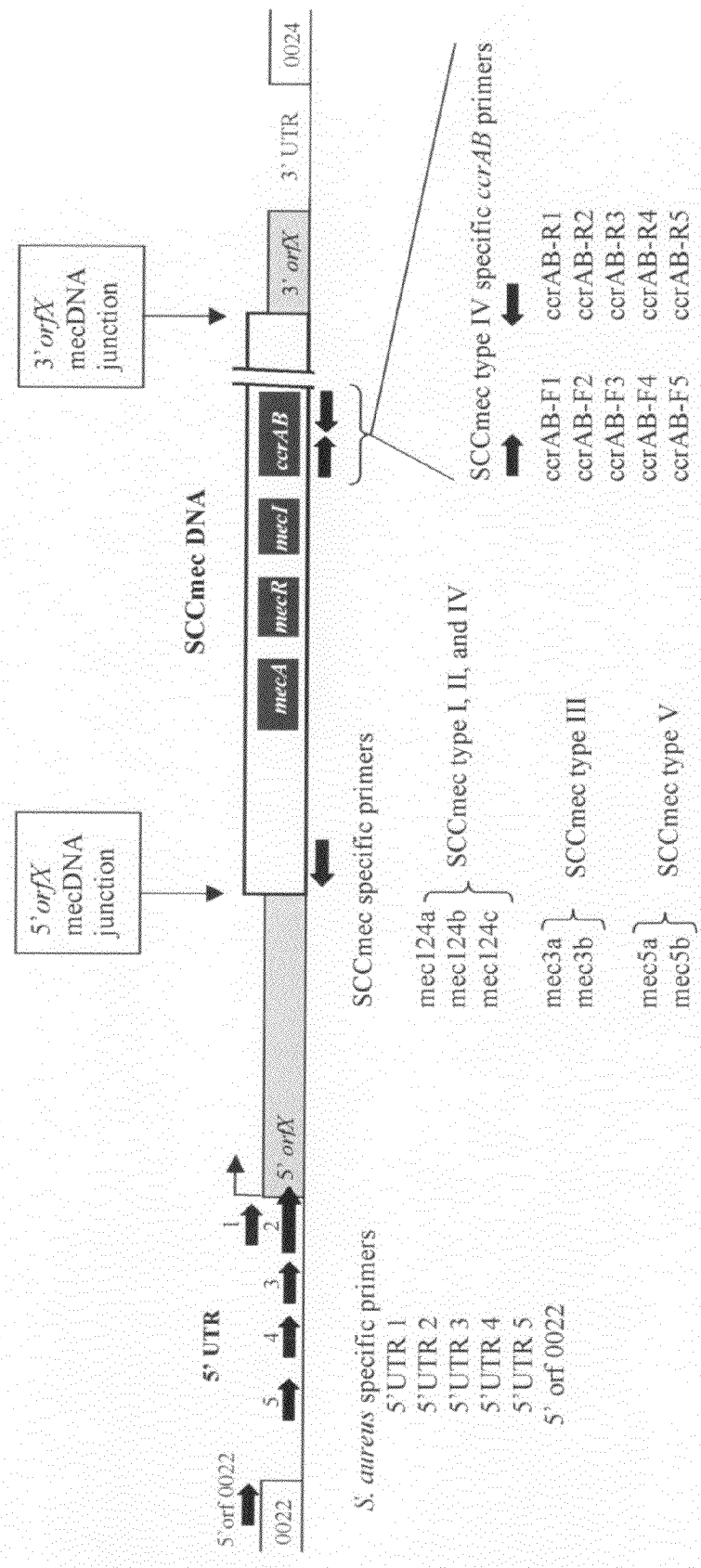
FIG. 1 depicts primer locations used in the development of the present assays found within the SCCmec DNA integration site in the orfX gene of *Staphylococcus aureus*. Noted that the *Staphylococcus aureus* specific forward primers are in the 5'UTR region and the SCCmec specific primers are downstream of the 5' orfX-mecDNA junction. SCCmec type IV specific primers are within the ccrAB gene.

Various terms used throughout this specification shall have the definitions set forth herein.

As used herein, the term "MRSA" refers to *Staphylococcus aureus* that is resistant to methicillin. MRSA contains the SCCmec transposon. MRSA can be subtyped into type I, type II, type III, type IV or type IV.

As used herein, the term "type I MRSA" refers to MRSA that contains SCCmec type I. It is positive for nuc gene and mecA gene.

As used herein, the term "type II MRSA" refers to MRSA that contains SCCmec type II. It is positive for nuc gene and mecA gene.

As used herein, the term "type III MRSA" refers to MRSA that contains SCCmec type III. It is positive for nuc gene and mecA gene.

As used herein, the term "type IV MRSA" refers to MRSA that contains SCCmec type III. It is positive for ccrAB gene, nuc gene and mecA gene.

As used herein, the term "HA-MRSA" refers to MRSA that contains SCCmec type I, II and III.

As used herein, the term "CA-MRSA" refers to MRSA that contains SCCmec type IV and is positive for PVL toxin.

As used herein, the term "orfX" refers to a *Staphylococcus aureus* specific gene and represents the site where SCCmec transposon integration occurs.

As used herein, the term "SCCmec DNA" refers to *Staphylococcus* Cassette Chromosome that contains the mecA, mecR, mecI and ccrAB genes.

As used herein, the term "mecA" refers to the methicillin resistant gene that encodes the low affinity penicillin binding protein 2 (PBP2a) and it renders the β-lactam resistance to the *Staphylococcus aureus*.

As used herein, the term "ccrAB" refers to the gene that encodes transposase/integrase and allows SCC to be a Mobile Genetic Element.

As used herein, the term "nuc" refers to the *Staphylococcus aureus* specific gene.

As used herein, "a" or "an" may mean one or more. As used herein, "another" may mean at least a second or more.

As used herein, the term "multiplex polymerase chain reaction" or "multiplex PCR" is a PCR reaction that consists of multiple primer sets within a single PCR mixture to produce amplicons of varying sizes that are specific to different DNA sequences. By targeting multiple genes at once, additional information may be gained from a single test run that otherwise would require several times the reagents and more time to perform.

As used herein, the term "primer" is an oligonucleotide or pair of oligonucleotides used to direct an activity to a region of nucleic acid. With PCR, a primer or pair of primers defines the area of the genome to be amplified.

As used herein, the term "OneSwab®" refers to a unique, non-invasive, highly stable specimen collection and transport platform proprietary to Medical Diagnostic Laboratories, LLC. OneSwab® platform consists of polyester fiber swab, liquid transport medium and polyethylene transport vial.

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

In describing example embodiments, specific terminology is employed for the sake of clarity. However, the embodiments are not intended to be limited to this specific terminology.

Currently, there are a number of methods to identify MRSA. These assays involve the determination if the bacterial species may contain a transposon called a Staphylococcal Cassette Chromosome (SCC), which contains the mecA resistance gene that results in β-lactam resistance. The SCCmec DNA integrates into a specific site within the orfX gene of the *Staphylococcus aureus* genome (See, FIG. 1). The SCCmec DNA contains a number of genes that are important in transposition of this mobile genetic element such as the ccrA and ccrB genes. The SCC also contains genes that are important for the expression of an alternative Penicillin Binding Protein 2 (PBP2' or PBP2a). The PBP2a is encoded by the mecA gene and regulated by the mecI and mecR proteins. The mecA protein when expressed in *Staphylococcus* provides the cell resistance to methicillin and other β-lactam type antibiotics.

The SCC can be found in a number of *Staphylococcus* species in addition to *Staphylococcus aureus*. These non-*Staphylococcus aureus* Staphylococcal species are commonly referred to as coagulase-negative *Staphylococcus* (CoNS), because they lack this aureus enzyme used for microbiology classification. The CoNS, such as *Staphylococcus epidermidis*, are common Staphylococcal species that are found as part of our natural skin flora. Therefore it is important to distinguish the presence of SCC in *Staphylococcus aureus* or MRSA from the other methicillin resistant CoNS (MRCoNS) species.

The present inventors discovered a novel method to determine whether a biological sample may contain *Staphylococcus aureus* and simultaneously determine if there is presence of types I, II, III, IV, or V of MRSA. Specifically, the present inventors designed a PCR assay where at least three (3) primer pairs are used. A first primer set allows the detection specifically for *Staphylococcus aureus* and detection of SCCmec types I, II and IV. A second primer set allows the detection of SCCmec type III. A third primer set allows the detection of SCCmec type IV.

With respect to the first primer set, the forward primers are specifically selected in the 5'UTR region. These forward primers, when generate amplicons in a PCR, confirms the presence of are *Staphylococcus aureus*. Hence, they represent *Staphylococcus aureus* specific primers. The reverse primers are specifically selected in a region downstream of the 5' orfX-mecDNA junction. Specifically, reverse primers (such as mec 124a, mec124b or mec124c) provides specificity towards SCCmec type I, II, and IV; and reverse primers (such as mec5a or mec5b) provides specificity towards SCCmec type V (See, Table 2 for details). Thus, the first primer set provides both the specificity for *Staphylococcus aureus* and MRSA subtypes I, II and IV.

With respect to the second primer set, the forward and reverse primer sets are specifically selected in the ccrAB gene region. The exemplary forward primer and reverse primer include ccrAB-F1 and ccrAB-R1 and ccrAB-F5 and ccrAB-R5. It is noteworthy that slight changes in the primer location results in failures (See, Table 6), indicating the unpredictable nature. Thus, the third primer set provides both the specificity for MRSA subtype IV.

With respect to the third primer set, the forward primers are common to that of the first primer set and are specifically selected in the 5'UTR region. The forward primers are *Staphylococcus aureus* specific primers. The reverse primers are specifically selected in a region downstream of the 5' orfX-mecDNA junction. Specifically, reverse primers (such as mec3a or mec3b) provides specificity towards SCCmec type III. Thus, the second primer set provides both the specificity for *Staphylococcus aureus* and MRSA subtype III.

In one embodiment, the PCR assay is a multiplex PCR assay where three (3) primer sets are used to differentiate types I, II, III, or IV of MRSA.

In another embodiment, the PCR assay further contains a fourth primer set, where the primer set is specific for the mecA gene contained within the transposon called a Staphylococcal Cassette Chromosome (SCC), and results in β-lactam resistance.

In another embodiment, the PCR assay further contains a fifth primer set, where the primer set is specific for the nuc gene contained within the SCC transposon.

Optionally, in another embodiment, an additional primer set may be added the PCR assay in the multiplex PCR assay to differentiate type V of MRSA. With respect to this additional primer set, the forward primers are specifically selected in the 5'UTR region and are *Staphylococcus aureus* specific (e.g., 5'UTR 3). The reverse primers are specifically selected in a region downstream of the 5' orfX-mecDNA junction. Specifically, reverse primers (such as mec5a or mec5b) provides specificity towards SCCmec type V. Thus, the optional primer set provides both the specificity for *Staphylococcus aureus* and MRSA subtype V.

Example embodiments are directed to methods of determining a subtype of methicillin-resistant *Staphylococcus aureus* (MRSA) in a biological sample of a mammal, such as a human. Methods include providing a biological sample of the mammal and performing a PCR analysis of the biological sample. The biological sample may include for example, cervical vaginal swab, nasal swab, skin swab, whole blood, saliva, urine, mucus, abscess, and other biological samples that may be extracted from a mammal according to known methods, for example by nasal swab. PCR analysis of the biological sample may be performed on the biological sample in its original form from the mammal, or the biological sample may be processed before PCR analysis of the sample.

One skilled in the art would recognize that because a biological sample often contain multiple microorganisms, its complex nature (contrary to a cultured isolates of a single strain microorganism, for example, a *Staphylococcus* isolate) often distort the PCR assays that do not have high specificity and sensitivity. The present assay provides high specificity and sensitivity using biological samples directly obtained from patients. Using DNA isolated from a biological sample, the present assay can confirm the presence of *Staphylococcus aureus* and distinguishes various subtypes of MRSA. The present assay is superior to all prior art PCR assays where they are limited to the use of cultured *Staphylococcus* isolates (i.e., following culture plating).

The present PCR analysis may include for example, the use of *Staphylococcus aureus* species-specific primers, primers located in the SCCmec DNA downstream of the 5' orfX-mecDNA junction, and SCCmec Type IV specific primers targeting the ccrAB genes.

Upon investigating the DNA sequence of the arm of the SCCmec DNA downstream of the 5' orfX mecDNA junction, the present inventors unexpectedly discovered that the SCC Types I, II, and IV are very similar which lead to the ability to use one reverse primer (mec124) to detect these three types (FIG. 8). Because the sequence of the SCC Type III is very different, this type requires its own reverse primer generating a 622 bp amplicon readily distinguishable from Type I (566 bp) and Type II/IV (668 bp) (FIG. 9).

According to non-limiting example embodiments, the PCR analysis of the biological sample may be a multiplex PCR assay where a plurality of primer pairs are used. Multiplexing of PCR reactions is common. Multiplexing allows an investigator to assay two or more different gene targets in a single reaction through the use of multiple probes or primers, each specific for its own target and each comprising a fluorescent moiety that emits at a unique wavelength. Multiplexing is possible with TaqMan® probes, Molecular Beacons, and Scorpions, as recognized by one skilled in the art. Due to its non-specific binding nature, SYBR® Green may not be amenable to multiplexing.

Typically, a PCR reaction is performed by one of two methods: comparison to a standard curve or comparison of threshold cycle (Ct) values. In the first of these methods, a standard curve of amplification products of a particular DNA is made based on amplification of a series of different, known amounts of a pre-selected nucleic acid. Amplification results of reactions performed on a target nucleic acid are then compared to the standard curve to obtain a quantity, and that quantity can be extrapolated to an amount of the target in the original sample.

In the Ct comparison method for quantitating PCR products, expression of a housekeeping gene (such as actin) is used as a standard against which amplification of a target nucleic acid is compared. Often, in this method, a comparison of expression of the target nucleic acid under two different conditions is performed to determine changes in expression patterns.

In one embodiment, the multiplex PCR assay is performed using at least three (3) primer pairs to identify types I, II, III and IV of MRSA.

In another embodiment, the three (3) primer pairs comprises: (1) a first primer pair that includes a forward primer 5'UTR 3 (SEQ ID NO: 3), and a reverse primer selected from the group consisting of mec124a (SEQ ID NO: 7), mec124b (SEQ ID NO: 8), and mec124c (SEQ ID NO: 9); (2) a second primer pair that includes a forward primer 5'UTR 3 (SEQ ID NO: 3) and a reverse primer selected from the group consisting of mec3a (SEQ ID NO: 10), and mec3b (SEQ ID NO: 11); and (3) a third primer pair that includes a forward primer ccrAB-F1 (SEQ ID NO: 14) and a reverse primer ccrAB-R1 (SEQ ID NO: 18), or a forward primer ccrAB-F5 (SEQ ID NO:21) and a primer ccrAB-R5 (SEQ ID NO: 23).

In accordance with the multiplex PCR assay, the first primer pair is specific for SCCmec types I, II and IV, thus permitting the generation of two amplicons with a similar size of about 668 bp (revealing SCCmectype II or IV), and one amplicon with a size of 566 bp (revealing SCCmec type I). The second primer pair is specific for SCCmec type III, permitting the generation of one amplicon with a size of 622 bp (revealing SCCmec type III). The third primer pair is specific type IV, permitting the generation of one amplicon with a size of 334 bp (revealing SCCmec type IV). The different molecular sizes of the amplicons can be conveniently be determined and analyzed in a gel, thus allowing the easy identification for types I, II, III or IV MRSA. The forward primer is selected in the 5'UTR region and it can be the same for the first, second and third primer pairs. A unique property of the forward primer (because of its location within the 5'UTR) conveniently provides *Staphylococcus*-specificity.

According to non-limiting example embodiments, the PCR analysis of the biological sample may be performed using at least a first primer pair that includes a forward primer 5'UTR 3 (SEQ ID NO: 3) and a reverse primer mec124b (SEQ ID NO: 8). According to example embodiments, the PCR analysis may be performed using a second primer pair that includes a forward primer 5'UTR 3 (SEQ ID NO: 3) and a reverse primer mec3b (SEQ ID NO: 11). According to example embodiments, the PCR analysis may be performed using a second primer pair that includes a third primer pair specific for SCCmec type IV, comprising a forward primer ccrAB-F1 (SEQ ID NO: 14) and a reverse primer ccrAB-R1 (SEQ ID NO: 18).

According to further non-limiting example embodiments, the PCR analysis of the biological sample may be performed using at least (1) a first primer pair that includes a forward primer 5'UTR 4 (SEQ ID NO: 4), and a reverse primer mec3a (SEQ ID NO: 10); and (2) a second primer pair comprising a forward primer ccrAB-F1 (SEQ ID NO: 14) and a reverse primer ccrAB-R1 (SEQ ID NO: 18), or a forward primer ccrAB-F5 (SEQ ID NO: 21) and a reverse primer ccrAB-R5 (SEQ ID NO: 23).

The PCR analysis provides a plurality of amplicons having different sizes. Example methods further include analyzing the PCR amplicons with respect to their different sizes so as to determine for type I, type II, type III or type IV MRSA that are present in the biological sample.

Detection or visualization of the PCR products after separation may be accomplished by techniques known to those skilled in the art. According to example techniques, visualization may be accomplished using ethidium bromide staining and UV light. These methods may include the use of labeled probes specific for the PCR products of interest.

The primer sets identified herein have been found to be superior to other tested primer sets, as discussed further below in the Examples. Examples of failed primer pairs are provided for example in Table 3.

Example embodiments may also include using at least one *Staphylococcus aureus* nuc primer pair in the PCR analysis. Thus, according to non-limiting example embodiments, the PCR analysis may further use a fourth *Staphylococcus aureus* specific nuc primer pair that includes a forward primer nuc F1 (SEQ ID NO: 26) and a reverse primer nuc R1 (SEQ ID NO: 27), prior to the detecting step.

Further example embodiments may include using at least one mecA primer pair in the PCR analysis to determine β-lactam resistance in the biological sample. Thus, according to non-limiting example embodiments, the PCR analysis may include the use of a fifth mecA primer pair comprising a forward primer mecA2 forward (SEQ ID NO: 24) and a reverse primer mecA2 reverse (SEQ ID NO: 25), prior to the detecting step.

Additional embodiments are directed to methods for screening populations to determine a subtype of MRSA in individuals of the population. By way of non-limiting example, pre-screening patients upon admission to a medical facility for MRSA may allow facilities to care for patients accordingly and to sanitize appropriately to prevent further spread of the MRSA and infection of others. Hospitals may not be the only population that may benefit from screening methods, however. Screening may be also advantageous in other populations such as schools or communities.

Example methods for screening may include obtaining at least one biological sample from an individual in a population; performing a PCR analysis of the biological sample, using the primer pairs provided herein, which PCR analysis provides a plurality of amplicons having different sizes; and analyzing the PCR amplicons with respect to their different sizes so as to determine for type I, type II, type III or type IV MRSA that are present in the biological sample.

As with other embodiments discussed herein, according to non-limiting example embodiments, the PCR analysis of the biological sample may be performed using at least (1) a first primer pair the includes a forward primer 5'UTR 3 (SEQ ID NO: 3), and at least one reverse primer selected from the group consisting of mec124a (SEQ ID NO: 7), mec124b (SEQ ID NO: 8), and mec124c (SEQ ID NO: 9); (2) a second primer pair that includes a forward primer 5'UTR 3 (SEQ ID NO: 3) and at least one reverse primer selected from the group consisting of mec3a (SEQ ID NO: 10), and mec3b (SEQ ID NO: 11); and (3) a third primer pair that includes a forward primer ccrAB-F1 (SEQ ID NO: 14) and a reverse primer ccrAB-R1 (SEQ ID NO: 18), or a forward primer ccrAB-F5 (SEQ ID NO:21 and a reverse primer ccrAB-R5 (SEQ ID NO: 23).

According to non-limiting example embodiments, the PCR analysis of the biological sample may be performed using at least a first primer pair that includes a forward primer 5'UTR 3 (SEQ ID NO: 3) and a reverse primer mec124b (SEQ ID NO: 8). According to example embodiments, the PCR analysis may be performed using a second primer pair that includes a forward primer 5'UTR 3 (SEQ ID NO: 3) and a reverse primer mec3b (SEQ ID NO: 11). According to example embodiments, the PCR analysis may be performed using a second primer pair that includes a third primer pair specific for SCC mec type IV, comprising a forward primer ccrAB-F1 (SEQ ID NO: 14) and a reverse primer ccrAB-R1 (SEQ ID NO: 18).

According to further non-limiting example embodiments, the PCR analysis of the biological sample may be performed using at least (1) a first primer pair that includes a forward primer 5'UTR 4 (SEQ ID NO: 4), and a reverse primer mec3a (SEQ ID NO: 10); and (2) a second primer pair comprising a forward primer ccrAB-F1 (SEQ ID NO: 14) and a reverse primer ccrAB-R1 (SEQ ID NO: 18), or a forward primer ccrAB-F5 (SEQ ID NO: 21) and a reverse primer ccrAB-R5 (SEQ ID NO: 23).

As with other example methods herein, example embodiments may also include using at least one *Staphylococcus aureus* nuc primer pair and/or at least one mecA primer pair in the PCR analysis.

Methods set forth herein may also include performing real-time PCR on the biological sample of an individual for canine herpes virus; and thereafter performing PCR analysis on the biological sample or on a different portion of the biological sample corresponding to an individual testing positive for canine herpes virus, to determine whether the individual has type IV MRSA.

MRSA strains are characterized by those that are associated with health care facilities such as hospitals and those that are found in the community. These strains are commonly referred to as hospital-associated MRSA (HA-MRSA) and community-associated MRSA (CA-MRSA). HA-MRSA strains have the SCCmec Type I, II, and III DNA. These strains are resistant not only to β-lactam antibiotics but tend to be resistant to other common antibiotics used in the health-care setting.

CA-MRSA strains have the SCC Type IV and V (type V is rare) and causes a more aggressive MRSA infection due to its association with virulence factors such as Panton-Valentine Leukocidin (PVL) gene and other factors that resist the cells of the human immune system. Currently, in order for a strain to be defined as CA-MRSA, it should possess the SCCmec DNA Type IV and the PVL gene. Although CA-MRSA strains are resistant to the β-lactam antibiotics and cause a more aggressive infection, they tend to be susceptible to most other antibiotics used in healthcare. Therefore it is important to determine HA-MRSA from CA-MRSA strains by determining the SCC molecular typing.

According to non-limiting example methods, if a biological sample in any of the methods herein is determined to have type IV MRSA, the method may further include performing a Panton-Valentine Leukocidin (PVL) real-time PCR assay on the biological sample, to determine if the type IV MRSA is Community Associated-MRSA (CA-MRSA).

Real-time PCR may be performed using exonuclease primers (TaqMan® probes). In such embodiments, the primers utilize the 5' exonuclease activity of thermostable polymerases such as Taq to cleave dual-labeled probes present in the amplification reaction (See, e.g., Wittwer, C. et al. *Biotechniques* 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

In another embodiment, real-time PCR methods may include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996).

Real-time PCR methods may also include the use of one or more hybridization probes, which may also be determined by those skilled in the art, in view of this disclosure. Exemplary probes such as the HEX channel and/or FAM channel probes, as understood by one skilled in the art.

A non-limiting example of a PVL assay is discussed in the Examples below. In Example 6, a real-time PCR assay to detect the PVL lukSF gene was designed and validated (See, Table 10; and FIGS. 21 and 22). This assay follows the SCC-mec Type IV determination by the multiplex MRSA detection and typing assay to characterize Community-Associated MRSA. In such an assay, the primers may include PVL F-2 (SEQ ID NO: 28), PVL R-2 (SEQ ID NO: 29), and PVL probe-2 (SEQ ID NO: 30).

Figure 22:
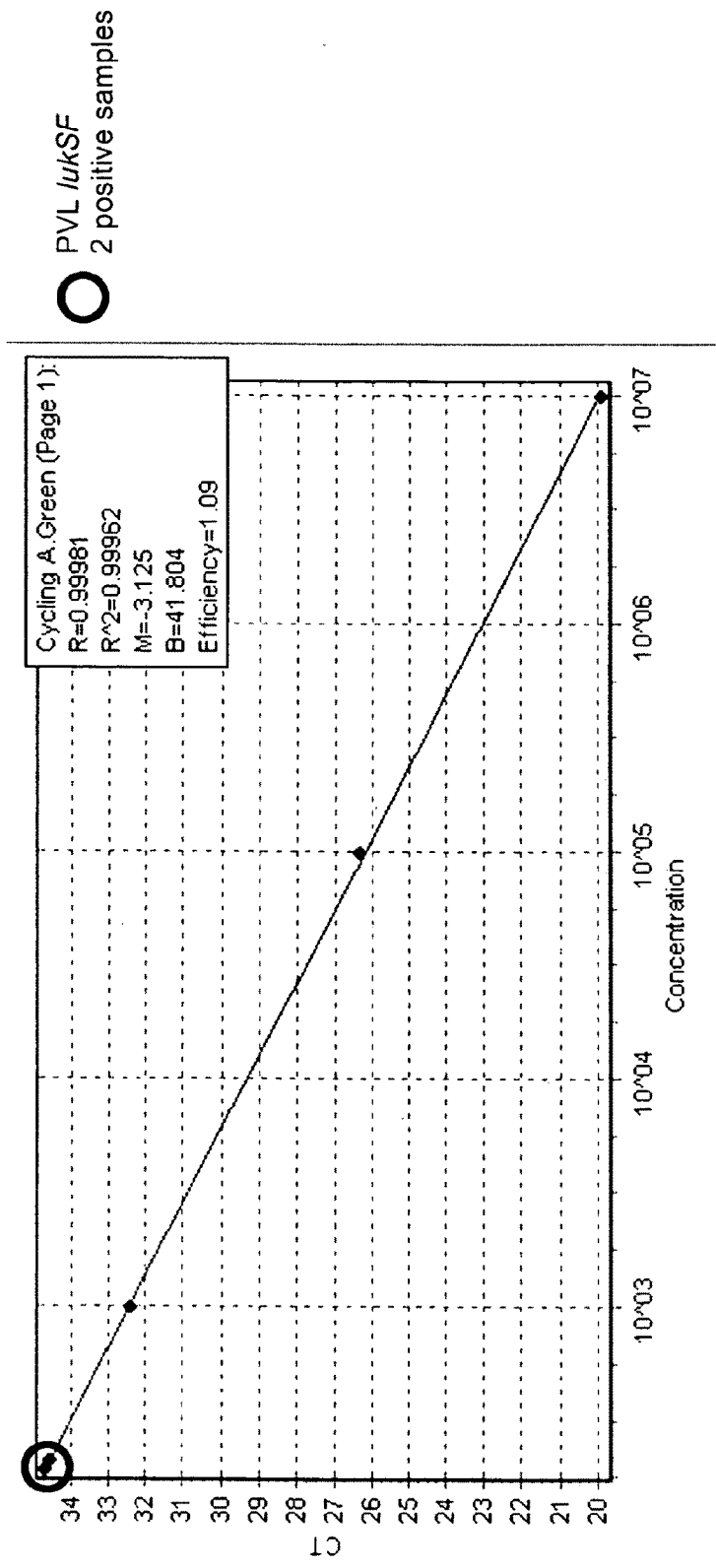
FIG. 22 depicts a standard curve of PVL real-time PCR. Both the standard curve and patient samples were tested in duplicate.

FIG. 22 depicts a standard curve of PVL real-time PCR. Both the standard curve and the patient samples were tested in duplicate.

Also provided herein are kits for determining a MRSA subtype in a mammal, which kits include at least one *Staphylococcus aureus* specific primer pair for detecting MRSA SCC Type, I, II, III and IV; and at least one SCCmec Type IV specific primer pair targeting the ccrAB genes.

Further provided herein are kits for performing the methods provided herein, including methods for determining a subtype of methicillin-resistant *Staphylococcus aureus* (MRSA) in a mammal. The kits may include for example one or more of the primers or primer pairs provided herein. Example kits may include instructions for using primer pairs in PCR reactions to determine if a mammal has type IV MRSA. Example kits may include at least one amplification primer selective for the mec gene complex and the ccr gene complex. Further examples may include at least one component for performing a Panton-Valentine Leukocidin (PVL) real-time PCR assay, to further determine if type IV MRSA is Community Associated-MRSA (CA-MRSA).

Example embodiments are also directed to methods of treating a mammal that include determining a subtype of MRSA in a biological sample by the methods herein, and administering an effective amount of at least one non β-lactam antibiotics to a mammal testing positive for Type IV MRSA. Upon detection of MRSA, MRSA can be treated with appropriate alternate antibiotics, such as glycopeptides (e.g., vancomycin, teichoplanin, telavancin, ramoplanin, decaplanin, linezolid, daptomycin and the like).

Administration of non β-lactam antibiotics may include administration in any suitable form and by any method known to those skilled in the art. For example, formulations may include tablets, capsules, IV formulations, etc, and may include various excipients or potentially other active ingredients. The appropriate formulation including at least one non β-lactam antibiotic(s) to be administered, may be determined by a skilled practitioner, such as a medical doctor, upon determining that a patient tests positive for Type IV MRSA using the present methods.

An "effective amount" for treating Type IV MRSA of a mammal testing positive for Type IV MRSA would be known by and/or may be determined by those skilled in the art, such as medical doctors. The determination of which antibiotic(s) to use in treating a patient, and in what amount, may be determined for example based on the age and/or weight of the mammal, other medications the mammal may be on or recently taken off of, other possible medical conditions, allergies, and other factors known to those skilled in the art, etc.

Further provided are isolated primers that may be used in the present methods and kits. By way of non-limiting example embodiment, provided herein are isolated SCCmec type IV specific ccrAB primers selected from the group consisting of ccrAB-F1 (SEQ ID NO: 14), ccrAB-F5 (SEQ ID NO: 21), ccrAB-R1 (SEQ ID NO: 18), and ccrAB-R5 (SEQ ID NO: 23).

Also provided are isolated oligonucleotide primers having a nucleotide sequence consisting essentially of a sequence selected from the group consisting of SEQ ID NO: 3, SEQ ID NO: 4, SEQ ID NO: 7, SEQ ID NO: 8, SEQ ID NO: 9, SEQ ID NO: 10, SEQ ID NO: 11, SEQ ID NO: 24, SEQ ID NO: 25, SEQ ID NO: 26, SEQ ID NO: 27, SEQ ID NO: 28, and SEQ ID NO: 29, which are the sequences for the following primers provided herein; 5'UTR 3, 5'UTR 4, mec124a, mec124b, mec124c, mec3a, mec3b, mecA2 forward, mecA2 reverse, nucF1, nucR1, PVL F2, and PVL R2. These primers may be made by methods known to those skilled in the art.

An advantage of the present invention is that the present assay provides a simple and sensitive screening assay for determining MRSA Types I-IV directly from a patient's biological sample. A majority of previously studies utilize MRSA clinical isolate clones for development of the screening assays. These assays, when applied to biological samples, may cross-react with non-*Staphylococcus aureus* species that contain SCCmec. This is because a biological sample obtained a patient often contains multiple species of microorganisms, including many non-*Staphylococcus aureus* species that may contain SCCmec. The present assay is superior because of our unique design of primer sets that offer simultaneous determination for *Staphylococcus aureus* species as well as MRSA subtyping.

Another advantage of the present invention is that while the present assay uses a biological sample directly obtained from patients, it can also uses clinical isolates. The present assay is proven to be a much sensitive and accurate test and has clinical application in diagnosis of patient populations.

Another advantage of the present invention is that the present assay involves a multiplex PCR assay having a minimum number of primer pairs which in turn reduce possible interference among the primer pairs (e.g., competition for reagents). The developed multiplex assay conveniently provides one (1) test reaction for simultaneous determination of various MRSA subtypes. It is well recognized by one skill in the art that use of multiple vials with multiple single primer pairs requires additional optimization and increases in cost and time. The present assay provides a physician rapid determination for Type IV MRSA in order for antibiotic intervention to occur and save human lives.

Another advantage of the present invention includes the use of an additional primer set that targets the PVL gene. The combined use of these primers provides additional information for MRSA subtyping and determination of community-associated MRSA (i.e., presence of PVL toxin).

Another advantage of the present invention includes the use of an additional primer set that targets the mecA gene. The presence of a mecA amplicon ensures the presence of mecA gene (which is responsible for methicillin resistance) and reduces the likely of false-positive results.

Another advantage of the present invention includes the use of an additional primer set that targets the nuc gene that provides confirmatory identity of *Staphylococcus aureus*.

The following examples were carried out using standard methods, and are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL STUDIES

Background

Currently there are a number of methods to identify Methicillin-Resistant *Staphylococcus aureus* (MRSA). These assays involve the determination of bacterial species may contain a transposon called a Staphylococcal Cassette Chromosome (SCC), which contains the mecA resistance gene that results in β-lactam resistance. The SCCmec DNA integrates into a specific site within the orfX gene of the *Staphylococcus aureus* genome (FIG. 1). The SCCmec DNA contains a number of genes that are important in transposition of this mobile genetic element such as the ccrA and ccrB genes. The SCC also contains genes that are important for the expression of an alternative Penicillin Binding Protein 2 (PBP2' or PBP2a). The PBP2a is encoded by the mecA gene and regulated by the mecI and mecR proteins. The mecA protein when expressed in *Staphylococcus* provides the cell resistance to methicillin and other β-lactam type antibiotics.

The SCC can be found in a number of *Staphylococcus* species in addition to *Staphylococcus aureus*. These non-*Staphylococcus aureus* Staphylococcal species are commonly referred to as coagulase-negative *Staphylococcus* (CoNS), because they lack this aureus enzyme used for microbiology classification. The CoNS, such as *Staphylococcus epidermidis*, are common Staphylococcal species that are found as part of our natural skin flora. It is important to distinguish the presence of SCC in *Staphylococcus aureus* or MRSA from the other methicillin-resistant CoNS (MR-CoNS) species.

Example 1

*Staphylococcus aureus* Detection and MRSA Types I, II, III, IV or V

In this study, we sought to design a conventional PCR assay that would specifically detect *Staphylococcus aureus* and simultaneously determine the types of MRSA. To achieve this goal, we selected a gene region that is *Staphylococcus aureus* specific and another gene region that allows differentiation of the SCC types. To that end, we chose the 5' untranslated region (5'UTR) of the orfX gene that could be specific for detection of *Staphylococcus aureus* (See, FIG. 1). We also chose the SCCmec specific region located at the left arm of the 5' orfX-mecDNA junction (See, FIG. 1). Forward primers were designed at the 5'UTR and reverse primers at the left arm of the 5' orfX-mecDNA junction. Our approach is unique and distinct from all prior art attempts. To the best of the present inventors' knowledge, there is no report suggesting the use of primer pairs in MRSA detection assay that offer simultaneous advantages of: (i) specificity for *Staphylococcus aureus*, and (ii) MRSA subtypes.

A) Forward Primers: We designed five (5) forward primers in the 5'UTR of the orfX gene, and one (1) forward primer at the 3' end of an open reading frame (orf0022) of the Newman strain genome sequence immediately upstream from orfX (FIG. 1). The nucleotide sequence for all the forward primers is listed in Table 1. All of these six (6) forward primers are specific for *Staphylococcus aureus* (FIG. 1, and Table 1).

TABLE 1

*Staphylococcus aureus* species-specific primers

| Primer Name | Nucleotide Sequence 5' to 3' | SEQ ID NO. |
|---|---|---|
| 5'UTR 1 | GTT GAT AAC AAT TTG GAG GAC CAA ACG AC | SEQ ID NO. 1 |
| 5'UTR 2 | GAT AAC AAT TTG GAG GAC CAA ACG | SEQ ID NO. 2 |
| 5'UTR 3 | CTT GTG GAT AAC TGG AAA GTT G | SEQ ID NO. 3 |
| 5'UTR 4 | GAG GGA ACA GTG TGA ACA AG | SEQ ID NO. 4 |
| 5'UTR 5 | CAC TAA AAA TCG GGC ATA AAT GTC AGG | SEQ ID NO. 5 |
| 5'orf0022 | CGA CTG TAC GAC GTA GAA AAG CTA GC | SEQ ID NO. 6 |

We showed the nucleotide sequences of the *Staphylococcus aureus* genome starting from the end of the orf0022 to the beginning of the orf0024 (See, FIG. 2). FIG. 2 also shows the exact placement of the six (6) forward primers designed to target at the 5' UTR and the 5' orf0022 of the Newman Genome sequence (NC009641). Newman genome sequence from 33241 to 34761 bp. The gDNA sequence of the SA0022 open reading frame (orf) to the 5' untranslated region (UTR) of orfX, to the orfX, to the 3' UTR of orfX, to the SA0024 orf. The site of the SCCmec DNA integration in the orfX gene is indicated in bold in FIG. 2. The transcriptional start site of orfX is indicated by the nucleotide sequence in italics atttggaggaccaaacgac (SEQ ID NO: 31). The translational start site is indicated by the bold atg. Primer sequences are indicated by underlines and 5' to 3' direction is indicated by the arrows.

B) Reverse Primers: We next designed a total of seven (7) reverse primers to anneal to the arm of the SCCmec DNA downstream of the 5' orfX-mecDNA junction (FIG. 1). The nucleotide sequence of these reverse primers is listed in Table 2 below. Out of the seven (7) reverse primers, three (3) were designed for SCCmec types I, II and IV, two (2) were designed for SCCmec type III and another two (2) were designed for SCCmec type V (FIG. 1).

(i) SCCmec Type I

Reverse Primers: mec124a, mec124b, and mec124c: We designed three (3) reverse primers for SCCmec type I. FIG. 3 shows the exact placement of the three (3) reverse primers (i.e., mec124a, mec124b, and mec124c) located at the left arm of the 5' orfX-mec DNA junction of the *Staphylococcus aureus* cassette chromosome (SCC) mec Type I (AB033763). Nucleotide sequence of the 5' end of the SCCmec DNA from SCC type I is located at the 5' orfX-mecDNA junction. Primers mec124a (SEQ ID NO:7), mec124b (SEQ ID NO:8), and mec124c (SEQ ID NO:9) were designed to hybridize to types I, II, and IV. The primer sequences are indicated by underlines and 5' to 3' direction is indicated by the arrows in FIG. 3.

(ii) SCCmec Type II

Reverse Primers: mec124a, mec124b, and mec124c: We designed three (3) reverse primers for SCCmec type II. FIG. 4 shows the exact placement of the three (3) reverse primers (i.e., mec124a, mec124b, and mec124c) located at the left arm of the 5' orfX-mec DNA junction of the *Staphylococcus aureus* cassette chromosome (SCC) mec Type II (D86934). Nucleotide sequence of the 5' end of the SCCmec DNA from SCC type II located at the 5' orfX mecDNA junction. Primers mec124a (SEQ ID NO:7), mec124b (SEQ ID NO:8), and mec124c (SEQ ID NO:9) were designed to hybridize to types I, II, and IV. The primer sequences are indicated by underlines and 5' to 3' direction is indicated by the arrows in FIG. 4.

(iii) SCCmec Type III

Reverse Primers: mec3a and mec3b: We designed two (2) reverse primers for SCCmec type III. FIG. 5 shows the exact placement of the two (2) reverse primers (i.e., mec3a and mec3b) located at the left arm of the 5' orfX-mec DNA junction of the *Staphylococcus aureus* cassette chromosome (SCC) mec Type III (AB037671). Nucleotide sequence of the 5' end of the SCCmec DNA from SCC type IIII located at the 5' orfX mecDNA junction. Primers mec3a (SEQ ID NO:10) and mec3b (SEQ ID NO:11) were designed to hybridize to type III only producing a product distinguishable from the other SCC types. The primer sequences are indicated by underlines and 5' to 3' direction is indicated by the arrows in FIG. 5.

(iv) SCCmec Type IV

Reverse Primers: mec124a, mec124b and mec124c: We designed three (3) reverse primers for SCCmec type IV. FIG. 6 shows the exact placement of the three (3) reverse primers (i.e., mec124a, mec124b, and mec124c) located at the left arm of the 5' orfX-mec DNA junction of the *Staphylococcus aureus* cassette chromosome (SCC) mec Type IV (AB063172). Nucleotide sequence of the 5' end of the SCCmec DNA from SCC type IV located at the 5' orfX mecDNA junction. Primers mec124a (SEQ ID NO:7), mec124b (SEQ ID NO:8), and mec124c (SEQ ID NO:9) were designed to hybridize to types I, II, and IV. The primer sequences are indicated by underlines and 5' to 3' direction is indicated by the arrows in FIG. 6.

(v) SCCmec Type V

Reverse Primers: mec5a and mec5b: We designed two (2) reverse primers for SCCmec type V. FIG. 7 shows the exact placement of the two (2) reverse primers (i.e., mec5a and mec5b) located at the left arm of the 5' orfX-mec DNA junction of the *Staphylococcus aureus* cassette chromosome (SCC) mec Type V (AB121219). Nucleotide sequence of the 5' end of the SCCmec DNA from SCC type V located at the 5' orfX mecDNA junction. Primers mec5a (SEQ ID NO:12) and mec5b (SEQ ID NO:13) were designed to hybridize to type V only producing a product distinguishable from the other SCC types. The primer sequences are indicated by underlines and 5' to 3' direction is indicated by the arrows in FIG. 7.

Example 2

A) Primer Pairs Used in Multiplex PCR Assay

Using the primer pairs (i.e., forward primers and reverse primers) designed in Example 1, we performed multiplex PCR reactions to detect MRSA and its typing. In these multiplex PCR reactions, three (3) primer pairs were used: (i) a first primer pair that included one of the 5'UTR forward primer and one of the reverse primer specific for SCCmec type I, II and IV; (ii) a second primer pair that included one of the 5'UTR forward primer and one of the reverse primer specific for SCCmec type III; and (iii) a third primer pair that included one of the 5'UTR forward primer and one of the reverse primer specific for SCCmec type V.

(i) SCCmec DNA Types I, II and IV

When we performed the nucleotide sequence alignments of the most prevalent types of SCCmec DNA, types I, II, III, and IV. It was determined that the left arm 5' end of the SCCmec DNA of types I, II, and IV were almost identical, except that there was a 102 bp deletion found within type I. We took advantage of such deletion and utilized it in the assay for type I identification by size discrimination (FIG. 8). Next, we specifically aligned the nucleotide sequence of the 5' end of the SCCmec DNA from SCC types I, II, and IV located at the left arm 5' orfX mecDNA junction (FIG. 8). Primers mec124a (SEQ ID NO:7), mec124b (SEQ ID NO:8), and mec124c (SEQ ID NO:9) were designed to hybridize to types I, II, and IV. The type I deletion allows for the size discrimination of type I from types II and IV. Primer sequences are indicated by underlines and 5' to 3' direction is indicated by the arrows as in FIG. 8.

(ii) SCCmec DNA Types III and V

Fortuitously, the present inventors discovered that only one (1) reverse primer would be needed to amplify type I, II and IV, while a separate reverse primer was needed to amplify type III due to significant sequence differences (See FIG. 9). An additional reverse primer was designed to anneal to SCC Type V. It should be noted that SCC Type V is a rare type of MRSA and was not tested in this study.

The nucleotide sequence alignment of the 5' end of the SCCmec DNA from SCC types I, II, IV and III located at the 5' orfX mecDNA junction is depicted in FIG. 9. As indicated above, types I, II, and IV sequences are identical except for the 102 bp deletion found in type I. Primers mec124a (SEQ ID NO:7), mec124b (SEQ ID NO:8), and mec124c (SEQ ID NO:9) were designed to hybridize to types I, II, and IV. The type I deletion allows for the size discrimination of type I from types II and IV. Type III sequence is significantly different (non-shaded nucleotides) from types I, II, and IV as shown by the shaded nucleotides which indicates sequence identity. Primers mec3a (SEQ ID NO:10) and mec3b (SEQ ID NO:11) were designed to hybridize to type III only producing a product distinguishable from the other SCC types. The primer sequences are indicated by underlines and 5' to 3' direction is indicated by the arrows (FIG. 9).

TABLE 2

Primers located with the SCCmec DNA downstream of the 5'orfX-mecDNA junction

| Primer Name | Nucleotide Sequence 5' to 3' | SEQ ID NO. |
|---|---|---|
| Primers for SCCmec types I, II, and IV | | |
| mec124a | GTC AAA AAT CAT GAA CCT CAT TAC TTA TG | SEQ ID NO. 7 |
| mec124b | GAC TGC GGA GGC TAA CTA TGT C | SEQ ID NO. 8 |
| mec124c | GAA CTT TGC TTC ACT ATA AGT ATT CAG | SEQ ID NO. 9 |
| Primers for SCCmec type III | | |
| mec3a | ATT TCA TAT ATG TAA TTC CTC CAC ATC TC | SEQ ID NO. 10 |
| mec3b | CGT ATG ATA TTG CAA GGT ATA ATC C | SEQ ID NO. 11 |
| Primers for SCCmec type V | | |
| mec5a | GCT TTT TCC ACT CCC ATT TCT TCC | SEQ ID NO. 12 |
| mec5b | CTA GTC TTC TTA ACC ATT CAC | SEQ ID NO. 13 |

B) Multiplex PCR Reactions

By using the three (3) primer pairs, we generated in the present multiplex PCR reactions several amplicons with different molecular sizes. The presence of these amplicons indicates that: (i) the specific detection of *Staphylococcus aureus*, and (ii) the varying sizes of the amplicons that permit simultaneous determination of the MRSA types.

(i) 5' UTR1 and mec124a Primer Pair Failed

Figure 10:
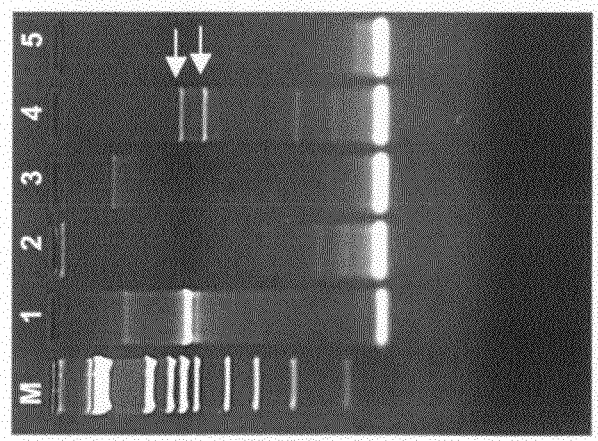
FIG. 10 depicts the representative results of a PCR reaction using the 5'UTR 1 (SEQ ID NO: 1) forward primer and the mec124a (SEQ ID NO:7) reverse primer.

In a multiplex PCR experiment using a prime pair (i.e., forward primer was 5' UTR1 (SEQ ID NO:1) and reverse primer (SEQ ID NO:7) was mec124a) and a positive control (i.e., MRSA SCCmec type II), we observed the generation of an amplicon in lane 1. Specifically, the PCR reaction was able to amplify the correct product from a MRSA SCC Type II strain (lane 1; 668 bp) (FIG. 10). The presence of this amplicon suggests that there was MRSA SCCmec type II (FIG. 10). However, this primer pair is not specific for MRSA, because it cross-reacted with MSSA strain (lane 4, FIG. 10). Therefore, this particular primer pair is not useful.

(ii) 5' orf0022 and mec124a Primer Pair Failed

Figure 11:
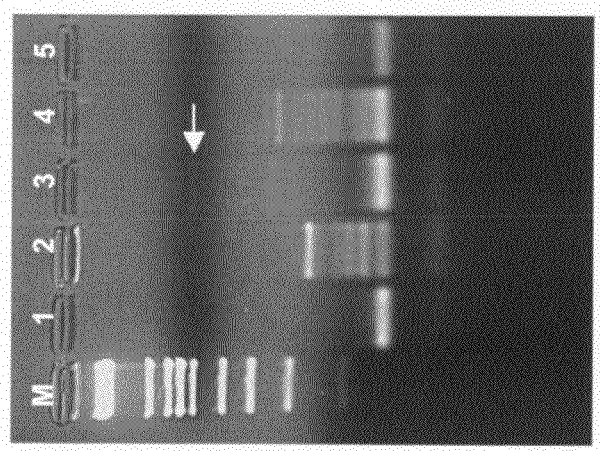
FIG. 11 depicts the representative results of PCR reactions using the 5' orf0022 forward primer and the mec124a (SEQ ID NO:7) reverse primer.

In another multiplex PCR experiment using another primer pair (i.e., forward primer was 5' orf0022 (SEQ ID NO:6) and reverse primer was mec124a (SEQ ID NO:7)) and a positive control (i.e., MRSA SCCmec type II), it failed to generate an amplicon specific for the MRSA SCCmec type II (lane 1, FIG. 11). Moreover this primer set cross-reacted with methicillin-resistant coagulase-negative *Staphylococcus epidermidis* (MRCoNS) (arrow, lane 3, FIG. 11) and produced some low molecular weight background bands (lane 2 and 4, FIG. 11). Therefore, our result indicates that this particular primer pair is not useful. These data indicate primer pair design in multiplex PCR reactions is highly unpredictable and that not every primer pair is not equivalent in terms of its ability to generate an amplicon.

(iii) Additional Primer Pairs That Failed

The present inventors performed additional multiplex PCR reactions and examined many possible permutations of primer pairs that we designed in Examples 1 and 2. Upon testing these primer pairs in multiplex PCR reactions, we surprisingly found that many of the primer pairs cannot function to detect *Staphylococcus aureus*, and majority of the designed primer pairs failed to differentiate SCC Types I, II, III, and IV (Table 3).

All the multiplex PCR reaction results using different forward and reverse primer combinations are summarized in Table 3. Notably, the basis for many of the PCR failure is found to include: (i) amplified only background bands with methicillin susceptible *Staphylococcus aureus* (MSSA) (FIG. 10); (ii) cross-reacted with MRCoNS (FIG. 11); and (iii) unable to amplify any products (FIG. 11).

TABLE 3

Failed primer pairs that had amplification issues upon testing Staphylococcus aureus species-specific primers with primers located with the SCCmec DNA downstream of the 5'orfX-mecDNA junction.

| 5' UTR Primer | SCCmec DNA Primer | Amplification Issues |
|---|---|---|
| 5' UTR 1 (SEQ ID NO: 1) | mec124a (SEQ ID NO: 7) | Faint Amplification, background |
| 5' UTR 1 (SEQ ID NO: 1) | mec3a (SEQ ID NO: 10) | No Amplification |
| 5' UTR 2 (SEQ ID NO: 2) | mec124a (SEQ ID NO: 7) | Background |
| 5' UTR 2 (SEQ ID NO: 2) | mec124b (SEQ ID NO: 8) | Background |
| 5' UTR 2 (SEQ ID NO: 2) | mec124c (SEQ ID NO: 9) | Background |
| 5' UTR 2 (SEQ ID NO: 2) | mec3a (SEQ ID NO: 10) | Background |
| 5' UTR 2 (SEQ ID NO: 2) | mec3b (SEQ ID NO: 11) | Background |
| 5' UTR 4 (SEQ ID NO: 4) | mec124a (SEQ ID NO: 7) | Background |
| 5' UTR 4 (SEQ ID NO: 4) | mec124b (SEQ ID NO: 8) | MRCoNS cross-reactivity |
| 5' UTR 4 (SEQ ID NO: 4) | mec124c (SEQ ID NO: 9) | No Amplification |
| 5' UTR 4 (SEQ ID NO: 4) | mec3b (SEQ ID NO: 11) | MRCoNS cross-reactivity |
| 5' UTR 5 (SEQ ID NO: 5) | mec124a (SEQ ID NO: 7) | Faint Amplification, Background |
| 5' UTR 5 (SEQ ID NO: 5) | mec3a (SEQ ID NO: 10) | No Amplification |
| 3' orf 0022 (SEQ ID NO: 6) | mec124a (SEQ ID NO: 7) | No Amplification |
| 3' orf 0022 (SEQ ID NO: 6) | mec3a (SEQ ID NO: 10) | No Amplification |

Example 3

In this series of study, we examined in a multiplex PCR reaction using a new primer pair (i.e., forward primer was 5' UTR3 (SEQ ID NO:3) and reverse primer was mec124b (SEQ ID NO:8). We used two (2) positive control strains (i.e., MRSA SCCmec type I and MRSA SCCmec type IV) in the PCR reaction.

(i) 5' UTR 3 (Forward Primer) and mec124a, b, and c (Reverse Primers): Differentiate SCCmec Type I and SCCmec Type IV To our surprise and unexpectedly, while many forward primers near the 5'UTR region have failed (Table 3), the forward primer 5'UTR 3 (SEQ ID NO: 3) was able to correctly amplify the target sequence, specifically detecting MRSA SCC Type I, II, and IV when used in combination with reverse primer mec124a (SEQ ID NO:7), mec124b (SEQ ID NO:8), or mec124c (SEQ ID NO:9) (FIG. 12).

Figure 12:
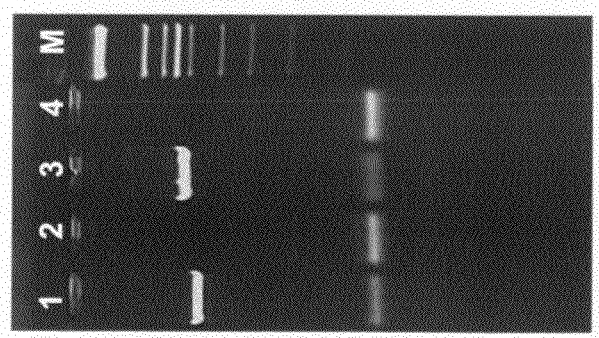
FIG. 12 depicts the representative results of PCR reactions using the 5'UTR 3 (SEQ ID NO: 3) forward primer and the mec124b (SEQ ID NO:8) reverse primer.

FIG. 12 summarizes the PCR reaction results. The forward primer 5'UTR 3 (SEQ ID NO: 3) and reverse primer mec124b (SEQ ID NO:8) was able to amplify the correct amplicon product from a MRSA SCC Type I strain (lane 1, FIG. 12) and another amplicon from a MRSA SCC Type IV strain (lane 3, FIG. 12). Note that the amplicon for the MRSA SCCmec type I was smaller than that of MRSA SCCmec type IV (500 bp vs. 668 bp). Thus, this particular primer pair permits the detection of *Staphylococcus aureus* and simultaneously allows the differentiation between MRSA SCCmec type I and MRSA SCCmec type IV.

In addition, we observed that this primer pair did not cross-react with MRSA SCCmec type III (lane 2, FIG. 12), indicating a high degree of specificity. We therefore concluded that this particular primer pair is useful for MRSA detection and typing.

Figure 13:
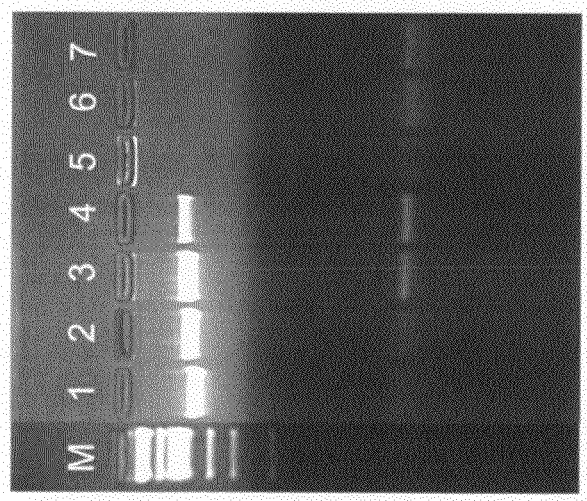
FIG. 13 depicts the representative results of PCR reactions using the 5'UTR 3 (SEQ ID NO: 3) forward primer and the mec124b (SEQ ID NO:8) and mec3b (SEQ ID NO:11) reverse primers.

(ii) 5' UTR 3 (Forward Primer) and mec3a, and mec3b (Reverse Primers): Differentiate SCCmec Type III In another study of multiplex PCR, we found that 5'UTR 3 (SEQ ID NO:3) (forward prier) was also able to amplify MRSA SCC Type III in combination with reverse primers mec3a (SEQ ID NO:10) and mec3b (SEQ ID NO:11), either individually or multiplexed with a mec124 reverse primer (FIG. 13).

(iii) 5' UTR 4 (Forward Primer) and mec3a (Reverse Primer): Differentiate SCCmec Type III In yet another study, we found that 5'UTR 4 (SEQ ID NO: 4) forward primer and mec3a (SEQ ID NO:10) reverse primer was able to amplify MRSA SCC Type III. However, the 5'UTR 4 (SEQ ID NO:4) primer did not work with the mec124 reverse primers for a successful multiplex reaction.

A summary of the PCR reaction results using the forward and reverse primer combinations that worked is provided in Table 4.

(iii) 5' UTR 3 (Forward Primer) and mec124b and mec3b (Reverse Primers): Differentiate SCCmec Type I, II, III, and IV FIG. 13 depicts multiplex PCR reactions using the 5'UTR 3 (SEQ ID NO:3) forward primer and the mec124b (SEQ ID NO:8) and mec3b (SEQ ID NO:11) reverse primers. The PCR reaction with forward primer 5'UTR 3 (SEQ ID NO: 3) and reverse primers, mec124b (SEQ ID NO:8) and mec3b (SEQ ID NO:11), was able to clearly amplify the correct product from MRSA SCC Type I, Type III, Type IV, and Type II strains (lanes 1, 2, 3, and 4, respectively, FIG. 13) without background. This primer pair did not cross-react with MSSA or MRCoNS (lane 5 and 6, FIG. 13).

TABLE 4

Primer pairs that successfully amplified upon testing *Staphylococcus aureus* species-specific primers with primers located with the SCCmec DNA downstream of the 5'orfX-mecDNA junction.

| 5' UTR Primer | SCCmec DNA Primer | Amplification |
|---|---|---|
| 5' UTR 3 (SEQ ID NO: 3) | mec124a (SEQ ID NO: 7) | Good |
| 5' UTR 3 (SEQ ID NO: 3) | mec124b (SEQ ID NO: 8) | Best |
| 5' UTR 3 (SEQ ID NO: 3) | mec124c (SEQ ID NO: 9) | Good |
| 5' UTR 3 (SEQ ID NO: 3) | mec3a (SEQ ID NO: 10) | Good |
| 5' UTR 3 (SEQ ID NO: 3) | mec3b (SEQ ID NO: 11) | Best |
| 5' UTR 4 (SEQ ID NO: 4) | mec3a (SEQ ID NO: 10) | Good |

Example 4

As discussed above, MRSA strains are characterized by those that are associated with health care facilities such as hospitals and those that are found in the community. These strains are commonly referred to as hospital-associated MRSA (HA-MRSA) and community-associated MRSA (CA-MRSA). CA-MRSA strains have the SCC Type IV and V (type V is rare) and causes a more aggressive MRSA infection due to its association with virulence factors such as Panton-Valentine Leukocidin (PVL) gene and other factors that resist the cells of the human immune system.

Currently, in order for a strain to be defined as CA-MRSA, it must possess the SCCmec DNA Type IV, or V and the PVL gene. Although CA-MRSA strains are resistant to the β-lactam antibiotics and cause a more aggressive infection, they tend to be susceptible to most other antibiotics used in healthcare. Therefore it is important to determine HA-MRSA from CA-MRSA strains by determining the SCC molecular typing.

It is important to determine the SCCmec DNA type before one can determine whether a MRSA strain is HA-MRSA or CA-MRSA. Upon investigating the DNA sequence of the arm of the SCCmec DNA downstream of the 5' orfX mecDNA junction, the present inventors found that the SCC Types I, II, and IV are very similar which lead to the ability to use one reverse primer (mec124) to detect these three types (FIG. 8).

Because the sequence of the SCC Type III is very different, this type requires its own reverse primer generating a 622 bp amplicon readily distinguishable from Type I (566 bp) and Type II/IV (668 bp)(FIG. 9).

Interestingly, the present inventors discovered that type I has a 102 bp deletion which lead to a smaller 566 bp amplicon which made type I distinguishable for type II and type IV (FIG. 8). Type II and Type IV are the same size (668 bp). In order to determine between Type II and Type IV, the present inventors designed primers (Table 5) that would specifically amplify the ccrAB gene from the Type IV SCCmec DNA (FIG. 1; see "SCCmec type IV specific ccrAB primers").

TABLE 5

SCCmec Type IV specific primers targeting the ccrAB genes.

| Primer Name | Nucleotide Sequence 5' to 3' | SEQ ID NO. |
|---|---|---|
| ccrAB F1 | GTT GAA AGA TGC AAA AGA AGG CA | SEQ ID NO. 14 |
| ccrAB F2 | CAG ACC TGA GCT CCA ACG TAT G | SEQ ID NO. 15 |
| ccrAB F3 | CGT GGT ATT TCA GGT AAA TCT ATG | SEQ ID NO. 16 |
| ccrAB F4 | GTA TCT ATG TAC GTG TAT CAA CAG | SEQ ID NO. 17 |
| ccrAB R1 | GTT AAT CAT TAG CTC GTG TTT ACT ATC | SEQ ID NO. 18 |
| ccrAB R2 | GTG ACA TAT CCT TTG TGA TTC | SEQ ID NO. 19 |
| ccrAB R3 | CAA ATT GAA TTT TGC CGA TAT AG | SEQ ID NO. 20 |
| ccrAB F5 | AGA TAG TAA ACA CGA GCT AAT GAT TAA C | SEQ ID NO. 21 |
| ccrAB R4 | CTA CAT GAA TAG TAA CGA ATA C | SEQ ID NO. 22 |
| ccrAB R5 | GCC GAA CAT ACT TTG GAA CCC TTG TTC CG | SEQ ID NO. 23 |

We aligned and compared the nucleotide sequence of the ccrAB gene that is different between the MRSA Type IV and Type II ccrAB genes (FIG. 14). Primers were designed to utilize these sequence differences so that they would anneal to and amplify Type IV specific ccrAB gene (FIGS. 14 and 15).

The nucleotide sequence alignment of the ccrAB gene is depicted in FIG. 14. The ccrAB gene was found within the two MRSA SCC type IV strains (AB06372 and AB097677) and two MRSA SCC type II strains (D86937 and AJ810120). Shaded nucleotides indicate sequence differences. Boxed shaded bold nucleotides indicate type IV specific differences. Primer sequences are indicated by underlines and 5' to 3' direction is indicated by the arrows.

Figure 15:
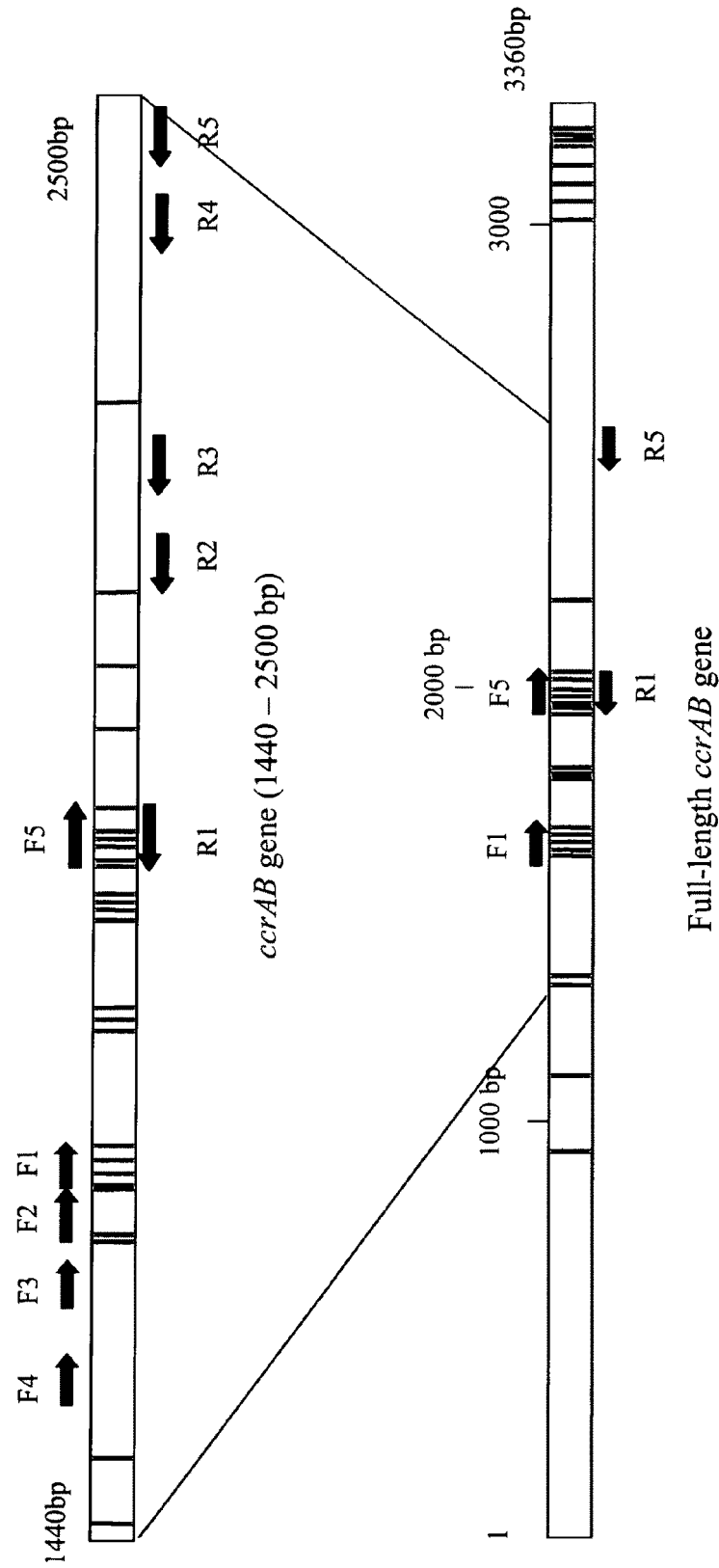
FIG. 15 depicts primer locations within the ccrAB gene of SCC Type IV.

FIG. 15 depicts primer locations within the ccrAB gene of SCC Type IV. The gray bars represents the location of nucleotide differences between SCC Type IV subtypes IVa (AB063172), IVb (AB063173), IVc (AB096217), IVd (AB097677) and SCC Type II subtypes IIa (D86937) and IIe (AJ810120) of the ccrAB gene.

We sought to design primers in order to amplify a product less than 500 bp to make it easily distinguishable from the SCC Typing amplicons. Upon testing these ccrAB forward and reverse primer pairs in PCR reactions, we found that the majority of the primer pairs either cross-reacted with SCC Type II ccrAB (FIG. 16) or amplified non-specific background bands from human DNA (FIG. 17).

A summary of the PCR results using different failed forward and reverse primer combinations is provided in Table 6.

Figure 16:
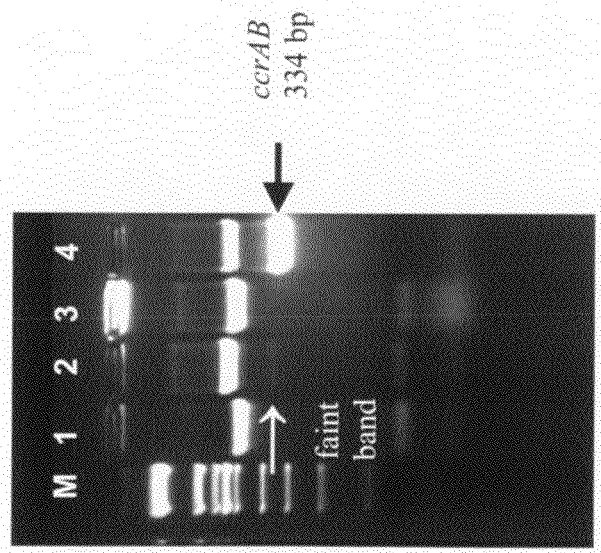
FIG. 16 depicts the representative results of PCR reactions using the ccrAB-F2 forward primer (SEQ ID NO:15) and the ccrAB-R1 reverse primer (SEQ ID NO:18). In particular.

The results of multiplex PCR reactions using the ccrAB-F2 forward primer (SEQ ID NO:15) and the ccrAB-R1 reverse primer (SEQ ID NO:18) are summarized in FIG. 16. The SCC Typing multiplex PCR reaction with forward primer 5'UTR 3 (SEQ ID NO:3) and reverse primers, mec124b (SEQ ID NO:8) and mec3b (SEQ ID NO:11) in combination with forward primer ccrAB-F2 (SEQ ID NO:15) and reverse primer ccrAB-R1 (SEQ ID NO:18) was able to amplify the correct SCC Type I, II, III, and IV amplicons (lanes 1, 2, 3, and 4, respectively, FIG. 16) and the ccrAB product from a MRSA SCC Type IV strain (lane 4, arrow, FIG. 16). However, these primers cross-reacted with the SCC Type II ccrAB (lane 2, arrow, FIG. 16).

The results of Multiplex PCR reactions using the ccrAB-F4 (SEQ ID NO:17) forward primer (SEQ ID NO:17) and the ccrAB-R1 reverse primer (SEQ ID NO:18) (FIG. 17). The SCC Typing multiplex PCR reaction with forward primer 5'UTR 3 (SEQ ID NO:3) and reverse primers, mec124b (SEQ ID NO:8) and mec3b (SEQ ID NO:11) in combination with forward primer ccrAB-F4 (SEQ ID NO:17) and reverse primer ccrAB-R1 (SEQ ID NO:18) was able to amplify the correct SCC Type I, II, III, and IV amplicons (lanes 11, 12, 13, and 14, respectively, FIG. 17) with the ccrAB product from a MRSA SCC Type IV strain was not amplified (lane 14). However, background amplification with human DNA was present (lanes 1 to 10, FIG. 17).

TABLE 6

Failed MRSA Type IV specific ccrAB primers that had amplification issues.

| Forward primer | Reverse primer | Amplification Issues |
|---|---|---|
| ccrAB-F2 (SEQ ID NO: 15) | ccrAB-R1 (SEQ ID NO: 18) | Type II background |
| ccrAB-F2 (SEQ ID NO: 15) | ccrAB-R2 (SEQ ID NO: 19) | Type II background |
| ccrAB-F2 (SEQ ID NO: 15) | ccrAB-R3 (SEQ ID NO: 20) | Type II background |
| ccrAB-F3 (SEQ ID NO: 16) | ccrAB-R1 (SEQ ID NO: 18) | Type II background |
| ccrAB-F4 (SEQ ID NO: 17) | ccrAB-R1 (SEQ ID NO: 18) | Type II background |
| ccrAB-F5 (SEQ ID NO: 21) | ccrAB-R4 (SEQ ID NO: 22) | Human DNA background |

(i) ccrAB-F1 and ccrAB-R1

Figure 18:
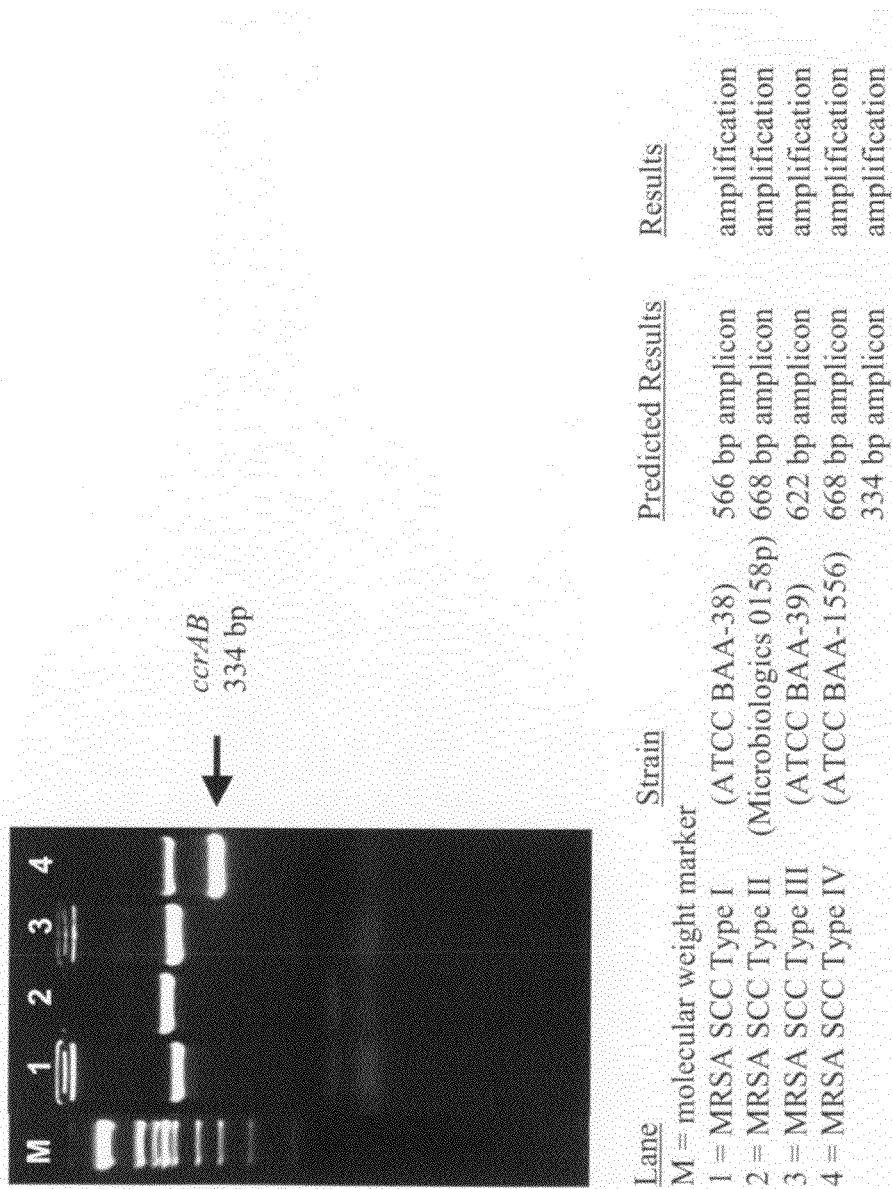
FIG. 18 depicts multiplex PCR reactions using the ccrAB-F1 (SEQ ID NO:14) forward primer and the ccrAB-R1 reverse primer (SEQ ID NO:18). In particular.

Two primer pairs (Table 7), ccrAB-F1 (SEQ ID NO:14) with ccrAB-R1 (SEQ ID NO:18) and ccrAB-F5 (SEQ ID NO:21) with ccrAB-R5 (SEQ ID NO:23), correctly amplified only the SCC Type IV ccrAB gene individually and in combination with the SCC typing multiplex reaction (FIG. 18).

FIG. 18 depicts the results of Multiplex PCR reactions using the ccrAB-F1 forward primer (SEQ ID NO:14) and the ccrAB-R1 reverse primer (SEQ ID NO:18). The SCC Typing multiplex PCR reaction with forward primer 5'UTR 3 (SEQ ID NO:3) and reverse primers, mec124b (SEQ ID NO:8) and mec3b (SEQ ID NO:11) in combination with forward primer ccrAB-F1 (SEQ ID NO:14) and reverse primer ccrAB-R1 (SEQ ID NO:18) was able to amplify the correct SCC Type I, II, III, and IV amplicons (lanes 1, 2, 3, and 4, respectively, FIG. 18) and the SCC Type IV specific ccrAB product from a MRSA SCC Type IV strain (lane 4, arrow, FIG. 18).

(ii) ccrAB-F5 and ccrAB-R5

The ccrAB-F5 (SEQ ID NO:21) and ccrAB-R1 (SEQ ID NO:18) are overlapping primers that utilize the same ccrAB sequence that contains a high degree of variation (FIGS. 14 and 15). We speculate that this ccrAB sequence polymorphism hot spot provides the SCC Type IV specificity.

TABLE 7

MRSA SCC Type IV specific ccrAB primers that successfully amplified.

| Forward primer | Reverse primer | Amplification Issues |
|---|---|---|
| ccrAB-F1 (SEQ ID NO: 14) | ccrAB-R1 (SEQ ID NO: 18) | Best; Size of amplicon best for descrimination in multiplex |
| ccrAB-F5 (SEQ ID NO: 21) | ccrAB-R5 (SEQ ID NO: 23) | Good; Size of amplicon too large for optimal descrimination in multiplex |

Example 5

Currently, PCR reactions that only amplify the orfX-SCC-mec DNA junction can result in false positives as the parts of the SCCmec DNA containing the mecA gene has the ability to recombine or loop out of the *Staphylococcus aureus* strain leaving behind an incomplete or non-functional SCCmec DNA (Rupp et al., 2006). Therefore, we chose to add to a multiplex PCR reaction with an additional primer pair (i.e., forward primer and reverse primer) to prevent the false positives (Table 8).

(i) Primer Pair (mecA2-For and mecA2 Rev) Specific for mecA

In this study, we chose two additional primers, mecA2-For (SEQ ID NO:24) (forward primer) and mecA2-Rev (SEQ ID NO:25) (reverse primer) were added to the multiplex mix to prevent these false positives (Table 8). The addition of the mecA primers into the multiplex reaction did not detract from the PCR efficiency and successfully amplified and determine the SCCmec Types, the type IV specific ccrAB amplicon, and the presence of the mecA gene (FIG. 19).

(ii) 5' UTR 3 and mec124b; 5'UTR 3 and mec3b; ccrAB-F1 and ccrAB-R1

The results of the multiplex PCR reactions with the addition of mecA primers are summarized in FIG. 19. The SCC Typing multiplex PCR reaction with forward primer 5'UTR 3 (SEQ ID NO:3) and reverse primers, mec124b (SEQ ID NO:8) and mec3b (SEQ ID NO:11) in combination with forward primer ccrAB-F1 (SEQ ID NO:14) and reverse primer ccrAB-R1 (SEQ ID NO:18) was able to amplify the correct SCC Type I, II, III, and IV amplicons (lanes 1, 2, 3, and 4, respectively) and the SCC Type IV specific ccrAB product from a MRSA SCC Type IV strain (lane 4).

The addition of the mecA forward and mecA reverse primers into the multiplex reaction successfully amplified and determine the SCCmec Types, the type IV specific ccrAB amplicon, and the presence of the mecA gene.

TABLE 8 mecA primers

| Primer Name | Nucleotide Sequence 5' to 3' | SEQ ID NO. |
|---|---|---|
| mecA2For | GTA CTG CTA TCC ACC CTC AAA CAG | SEQ ID NO. 24 |
| mecA2Rev | GAA CCT GGT GAA GTT GTA ATC TGG | SEQ ID NO. 25 |

Example 6

(i) Primer Pair (nuc F1 and nuc R1) Specific for nuc

Primers that will amplify the *Staphylococcus aureus* nuclease gene or nuc gene were added to the multiplex (Table 9). This provides an additional level of control to the MRSA detection assay to assure that *Staphylococcus aureus* is present in the sample. Also, this provides the ability to detect MSSA, since this strain would result in no amplification with the multiplex assay without the nuc primers. The addition of the nuc primers into the multiplex reaction did not detract from the PCR efficiency and successfully amplified and determine the SCCmec Types, the type IV specific ccrAB amplicon, the presence of the mecA gene, and the presence of the *Staphylococcus aureus* specific nuc gene (FIG. 20).

The results of multiplex PCR reactions with the addition of nuc primers are summarized in FIG. 20. The SCC Typing multiplex PCR reaction with forward primer 5'UTR 3 (SEQ ID NO:3) and reverse primers, mec124b (SEQ ID NO:8) and mec3b (SEQ ID NO:11), forward primer ccrAB-F1 (SEQ ID NO:14) and reverse primer ccrAB-R1 (SEQ ID NO:18), forward primer mecA2-For (SEQ ID NO:24) and reverse primer mecA2-Rev (SEQ ID NO:25) was able to amplify the correct SCC Type I, II, III, and IV amplicons (lanes 1, 2, 3, and 4, respectively, FIG. 20), the SCC Type IV specific ccrAB product from a MRSA SCC Type IV strain (lane 4, FIG. 20), and the mecA gene.

The addition of the nuc forward (nuc F1, SEQ ID NO:26) and nuc reverse (nuc R1, SEQ ID NO:27) primers into the multiplex reaction successfully amplified and determine the SCCmec types, the type IV specific ccrAB amplicon, the presence of the mecA gene, and an additional *Staphylococcus aureus* specific nuc control.

Figure 23:
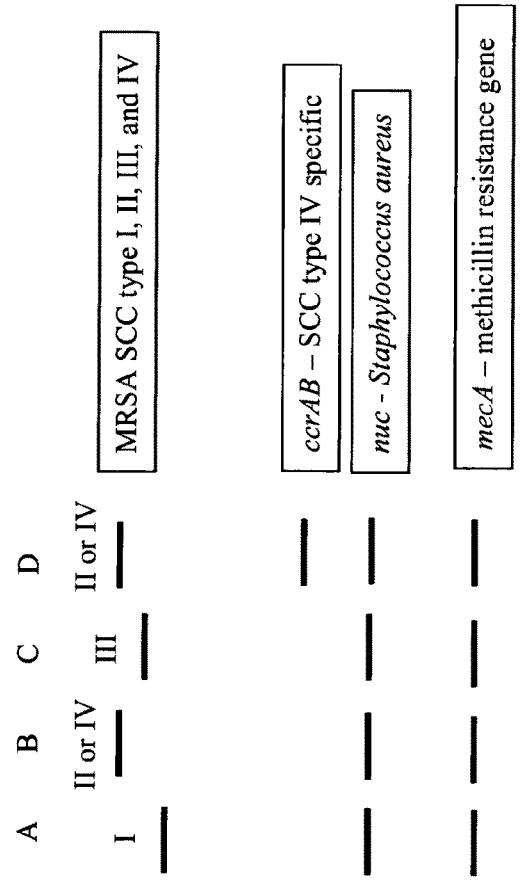
FIG. 23 is a diagram depicting an example of Methicillin-Resistant *Staphylococcus aureus* (MRSA) Positive Results.

FIG. 23 also shows Methicillin Resistant *Staphylococcus aureus* (MRSA) Positive Results using a multiplex PCR reaction with forward primer 5'UTR 3 (SEQ ID NO:3) and reverse primers, mec124b (SEQ ID NO:8) and mec3b (SEQ ID NO:11), forward primer ccrAB-F1 (SEQ ID NO:14) and reverse primer ccrAB-R1 (SEQ ID NO:18), forward primer mecA2-For (SEQ ID NO:24) and reverse primer mecA2-Rev (SEQ ID NO:25) was able to amplify the correct SCC Type I, II, III, and IV amplicons (lanes 1, 2, 3, and 4, respectively), the SCC Type IV specific ccrAB product from a MRSA SCC Type IV strain (lane 4), and the mecA gene. Also included were nuc forward (nuc F1, SEQ ID NO:26) and nuc reverse (nuc R1, SEQ ID NO:27) primers.

TABLE 9

*Staphylococcus* specific nuc gene primers

| Primer Name | Nucleotide Sequence 5' to 3' | SEQ ID NO. |
|---|---|---|
| nuc F1 | GTG CTG GCA TAT GTA TGG | SEQ ID NO. 26 |
| nuc R1 | CGC TTT AAT TAA TGT CGC AGG | SEQ ID NO. 27 |

Example 7

As stated in Example 4, CA-MRSA strains have the SCC Type IV and V (type V is rare) and causes a more aggressive MRSA infection due to its association with virulence factors such as Panton-Valentine Leukocidin (PVL) gene and other factors that resist the cells of the human immune system. Currently, in order for a strain to be defined as CA-MRSA, it should possess the SCC Type IV, or V, and the PVL gene. Although CA-MRSA strains are resistant to the β-lactam antibiotics and cause a more aggressive infection, they tend to be susceptible to most other antibiotics used in healthcare. Therefore it is important to determine HA-MRSA from CA-MRSA strains by determining the SCC molecular typing.

(i) Real-Time PCR Assay for PVL Gene

Figure 21:
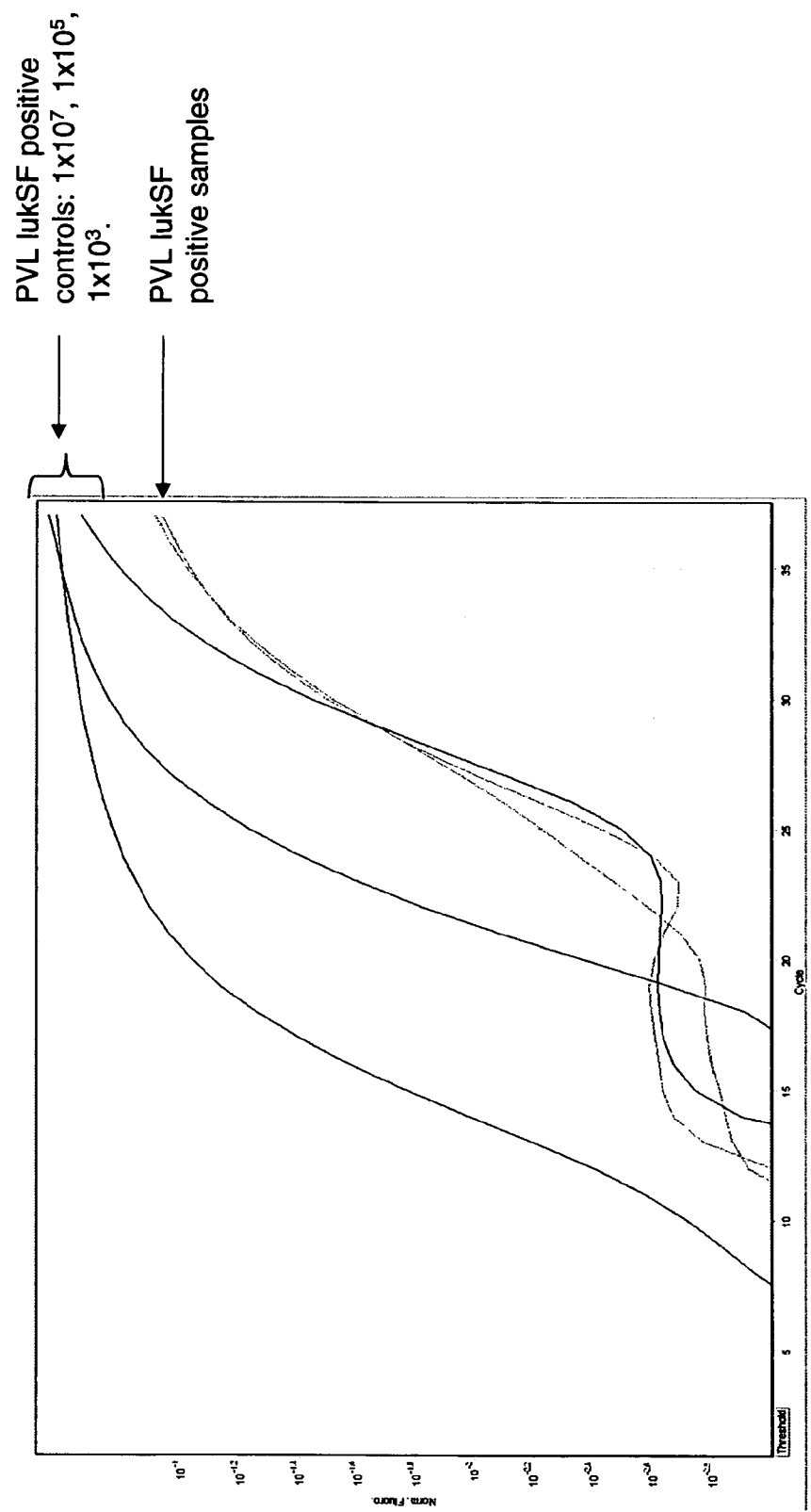
FIG. 21 depicts the results of a Panton-Valentine Leukocidin real-time PCR assay designed to detect the PVL lukSF gene. This assay follows the SCCmec Type IV determination by the multiplex MRSA detection and typing assay to characterize Community-Associated MRSA.

A real-time PCR assay to detect the PVL lukSF gene was designed and validated (Table 10; FIGS. 21 and 22). This assay follows the SCCmec Type IV determination by the multiplex MRSA detection and typing assay to define CA-MRSA.

FIG. 21 depicts Panton-Valentine Leukocidin real-time PCR. A real-time PCR assay was designed to detect the PVL lukSF gene. This assay follows the SCCmec Type IV determination by the multiplex MRSA detection and typing assay to characterize Community-Associated MRSA.

(ii) Standard Curve for PVL Real-Time PCR

FIG. 22 depicts a standard curve of PVL real-time PCR. Both the standard curve and patient samples were tested in duplicate.

TABLE 10

CA-MRSA Panton-Valentine Leukocidin lukS/lukF primers and probe.

| Primer Name | Nucleotide Sequence 5' to 3' | SEQ ID NO. |
|---|---|---|
| PVL F-2 | AGT CAA ATC ATC AGT TGT TAC ATC A | SEQ ID NO. 28 |
| PVL R-2 | ATC GGA ATC TGA TGT TGC AG | SEQ ID NO. 29 |
| PVL probe-2 | 56-FAM/ATG CAG CTC AAC ATA TCA CAC CTG TA/3BHQ_1 | SEQ ID NO. 30 |

Example 8

(i) Multiplex PCR Assay Protocol

This Example provides a protocol for a non-limiting example assay, which may be used to determine a type of methicillin-resistant *Staphylococcus aureus* (MRSA) in a biological sample according to present methods. PCR reactions are performed in 30 ml reaction volumes using the following PCR parameters:

TABLE 11

PCR parameters

| Component | Stock | Final concentration |
|---|---|---|
| Extracted DNA | 0.2 µg/ml | 10 µl |
| Biorad qPCR Mastermix* | 2X | 12.5 µl |
| Sa5pUTR 3 (SEQ ID NO: 3) | 30 µM | 0.6 µl |
| mec 124b (SEQ ID NO: 8) | 30 µM | 0.1 µl |
| mec 3b (SEQ ID NO: 11) | 30 µM | 0.6 µl |
| SccIV ccrAB F1 (SEQ ID NO: 14) | 30 µM | 0.2 µl |
| SccIV ccrAB R1 (SEQ ID NO: 18) | 30 µM | 0.2 µl |
| nuc F1 (SEQ ID NO: 26) | 30 µM | 0.2 µl |
| nuc R1 (SEQ ID NO: 27) | 30 µM | 0.2 µl |
| mecA2 forward (SEQ ID NO: 24) | 30 µM | 0.1 µl |
| mecA2 reverse (SEQ ID NO: 25) | 30 µM | 0.1 µl |
| ddH$_2$O | | 5.2 µl |

*2X reaction buffer containing dNTP/dUTP, iTaq, MgCl$_2$, UNG and stabilizers

Tubes may be reserved for controls. For example, the positive controls may be from plasmid constructs pmecI CLO, pmecII CLO, pmecIII CLO, and pmec IV CLO. Additionally, each positive control contains both the pnucCLO and the pmecACLO plasmid construct. The mecIV specific positive control also contains a third control from the pccrABCLO plasmid construct.

Profile conditions may be carried out on the Rotorgene 3000 or Rotorgene 6000 by the following steps:

TABLE 12

PCR reaction conditions

| Step | Time | Temp | Reason |
|---|---|---|---|
| Hold | 3 minutes | 94° C. | Initial Denaturation |
| Cycling (40 cycles) | 30 seconds | 94° C. | Denaturation |
| | 60 seconds | 70° C. Touchdown 1° C. for 12 cycles | Annealing |
| | 60 seconds | 72° C. | Extension |
| Hold | 10 minutes | 72° C. | Final Extension |

*Note: PCR products should be saved.

5'UTR 3 (SEQ ID NO:3) and reverse primers, mec124b (SEQ ID NO:8) and mec3b (SEQ ID NO:11), forward primer ccrAB-F1 (SEQ ID NO:14) and reverse primer ccrAB-R1 (SEQ ID NO:18), forward primer mecA2-For (SEQ ID NO:24) and reverse primer mecA2-Rev (SEQ ID NO:25) was able to amplify the correct SCC Type I, II, III, and IV amplicons (lanes 1, 2, 3, and 4, respectively), the SCC Type IV specific ccrAB product from a MRSA SCC Type IV strain (lane 4), and the mecA gene. Also included were nuc forward (nuc F1, SEQ ID NO:26) and nuc reverse (nuc R1, SEQ ID NO:27) primers.

The protocol includes loading 20 µL of PCR product on a 2.5% agaraose gel using 5 µL of 5× loading dye for each sample and 10 µL of 100 bp ladder in the first lane. Run the gel at 80 volts for 120 minutes.

Amplification at any of the type specific correct base pairs, along with the nuc and mecA indicates a positive sample for Methicillin resistance. For mec IV, an additional amplification of the SCCmecIV ccrAB base pair deems a positive sample for Methicillin resistance.

Figure 24:
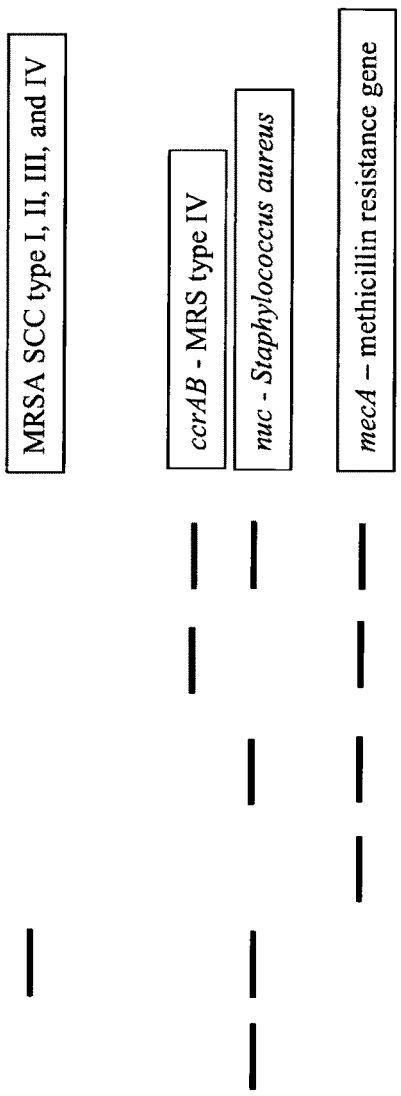
FIG. 24 is a diagram showing an example of MRSA negative results. MRSA SCC type negative and nuc positive indicate the presence of Methicillin-Susceptible *Staphylococcus aureus* (MSSA).

FIG. 24 depicts Examples of MRSA Negative Results: MRSA SCC type Negative and nuc Positive PCR results indicate the presence of Methicillin-Susceptible *Staphylococcus aureus* (MSSA).

Although the present inventions have been described in example embodiments, additional modifications and variations would be apparent to those skilled in the art. It is therefore to be understood that the inventions herein may be practiced other than as specifically described. The present embodiments should be considered in all respects as illustrative and not restrictive. Accordingly, it is intended that such changes and modifications fall within the scope of the present inventions as defined by the claims appended hereto. All patents, patent applications, publications and other materials cited herein are hereby incorporated by reference in their entirety.

What is claimed is:

1. A method of determining a type of methicillin-resistant *Staphylococcus aureus* (MRSA) in a biological sample, comprising the steps of
   (a) providing a biological sample;
   (b) performing a multiplex PCR analysis of the biological sample, using
      (i) a first primer pair comprising a forward primer 5'UTR 3 (SEQ ID NO: 3) and a reverse primer mec124b (SEQ ID NO: 8),
      (ii) a second primer pair comprising a forward primer 5'UTR 3 (SEQ ID NO: 3) and a reverse primer mec3b (SEQ ID NO: 11), and
      (iii) third primer pair specific for SCCmec type IV, comprising a forward primer ccrAB-F1 (SEQ ID NO: 14) and a reverse primer ccrAB-R1 (SEQ ID NO: 18),
         wherein the PCR analysis provides a plurality of amplicons having different sizes; and
   (c) determining the PCR amplicons with respect to their different sizes so as to reveal if type I, type II, type III or type IV MRSA is present in the biological sample.

2. The method of claim 1, wherein the PCR analysis in step (b) further comprises using a nuc-specific primer pair comprising a forward primer nuc F1 (SEQ ID NO: 26) and a reverse primer nuc R1 (SEQ ID NO: 27).

3. The method of claim 1, wherein the PCR analysis in step (b) further comprises using a mecA primer pair comprising a forward primer mecA2 forward (SEQ ID NO: 24) and a reverse primer mecA2 reverse (SEQ ID NO: 25).

4. A method of determining a type of methicillin-resistant *Staphylococcus aureus* (MRSA) in a biological sample, comprising the steps of:
   (a) providing a biological sample;
   (b) performing a multiplex PCR analysis of the biological sample, using
      (i) a first primer pair comprising a forward primer 5'UTR 3 (SEQ ID NO: 3), and at least one reverse primer selected from the group consisting of mec124a (SEQ ID NO: 7), mec124b (SEQ ID NO: 8), and mec124c (SEQ ID NO: 9),
      (ii) a second primer pair comprising a forward primer 5'UTR 3 (SEQ ID NO: 3), and at least one reverse primer selected from the group consisting of mec3a (SEQ ID NO: 10), and mec3b (SEQ ID NO: 11), and
      (iii) a third primer pair comprising a forward primer ccrAB-F1 (SEQ ID NO: 14) and a reverse primer ccrAB-R1 (SEQ ID NO: 18), or a forward primer ccrAB-F5 (SEQ ID NO:21 and a reverse primer ccrAB-R5 (SEQ ID NO: 23);
         wherein the PCR analysis provides a plurality of amplicons having different sizes; and
   (c) determining the PCR amplicons with respect to their different sizes so as to reveal if type I, type II, type III or type IV MRSA is present in the biological sample.

5. The method of claim 4, wherein said biological sample is selected from the group consisting of cervical vaginal swab, pap smear and nasal swab.

6. The method of claim 4, wherein said first primer pair comprises a forward primer 5'UTR 3 (SEQ ID NO: 3) and a reverse primer mec124b (SEQ ID NO: 8).

7. The method of claim 4, wherein said second primer pair comprises a forward primer 5'UTR 3 (SEQ ID NO: 3) and a reverse primer mec3b (SEQ ID NO: 11).

8. The method of claim 4, wherein said third primer pair comprises a forward primer ccrAB-F1 (SEQ ID NO: 14) and a reverse primer ccrAB-R1 (SEQ ID NO: 18).

9. The method of claim 4, wherein the PCR analysis further uses at least one mecA primer pair to determine β-lactam resistance in the biological sample.

10. The method of claim 9, wherein said mecA primer pair comprises a forward primer mecA2 forward (SEQ ID NO: 24) and a reverse primer mecA2 reverse (SEQ ID NO: 25).

11. The method of claim 4, wherein the PCR analysis further uses a *Staphylococcus aureus* nuc primer pair.

12. The method of claim 11, wherein said *Staphylococcus aureus* nuc primer pair comprises a forward primer nuc F1 (SEQ ID NO: 26) and a reverse primer nuc R1 (SEQ ID NO: 27).

13. The method of claim 4, wherein if said biological sample is determined to have type IV, MRSA, said method further comprises performing a Panton-Valentine Leukocidin (PVL) real-time PCR assay on the biological sample, to determine if the type IV MRSA is Community Associated-MRSA (CA-MRSA).

14. A method of determining a type of methicillin-resistant *Staphylococcus aureus* (MRSA) in a biological sample, comprising the steps of:
   (a) providing a biological sample;
   (b) performing a multiplex PCR analysis of the biological sample, using
      (i) a first primer pair comprising a forward primer 5'UTR 4 (SEQ ID NO: 4), and a reverse primer mec3a (SEQ ID NO: 10), and
      (ii) a second primer pair comprising a forward primer ccrAB-F1 (SEQ ID NO: 14) and a reverse primer ccrAB-R1 (SEQ ID NO: 18), or a forward primer ccrAB-F5 (SEQ ID NO: 21) and a reverse primer ccrAB-R5 (SEQ ID NO: 23);
         wherein the PCR analysis provides a plurality of amplicons having different sizes; and
   (c) determining the PCR amplicons with respect to their different sizes so as to reveal if type I, type II, type III or type IV MRSA is present in the biological sample.

15. The method of claim 14, wherein the PCR analysis further uses at least one mecA primer pair to determine β-lactam resistance in the biological sample.

16. The method of claim 14, wherein the PCR analysis further uses a *Staphylococcus aureus* nuc primer pair.

17. The method of claim 14, further comprising performing a Panton-Valentine Leukocidin (PVL) real-time PCR assay on the biological sample, to determine if the type IV MRSA is Community Associated-MRSA (CA-MRSA).

* * * * *